(12) United States Patent
Kondou et al.

(10) Patent No.: US 8,519,150 B2
(45) Date of Patent: Aug. 27, 2013

(54) π-ELECTRON CONJUGATED COMPOUND, MANUFACTURING METHOD THEREFOR, AND π-ELECTRON CONJUGATED POLYMER OBTAINED USING SAME

(75) Inventors: Yoshirou Kondou, Tsukuba (JP); Kirihiro Nakano, Tsukuba (JP); Tomiaki Otake, Tsukuba (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 13/124,073

(22) PCT Filed: Oct. 16, 2009

(86) PCT No.: PCT/JP2009/067936
§ 371 (c)(1),
(2), (4) Date: Apr. 13, 2011

(87) PCT Pub. No.: WO2010/044470
PCT Pub. Date: Apr. 22, 2010

(65) Prior Publication Data
US 2011/0201777 A1  Aug. 18, 2011

(30) Foreign Application Priority Data

Oct. 17, 2008  (JP) ................................. 2008-268942
Mar. 19, 2009  (JP) ................................. 2009-068682

(51) Int. Cl.
*C07D 495/04* (2006.01)
*C07D 513/04* (2006.01)
*C07D 513/14* (2006.01)

(52) U.S. Cl.
USPC ..... 548/303.1; 548/110; 548/134; 548/303.7; 528/367; 345/105; 359/270; 252/586

(58) Field of Classification Search
USPC .......................................... 548/303.1, 303.7
See application file for complete search history.

(56) References Cited

U.S. PATENT DOCUMENTS

| | | | |
|---|---|---|---|
| 2004/0119049 A1 | 6/2004 | Heeney et al. | |
| 2007/0278453 A1 | 12/2007 | Zahn et al. | |
| 2007/0282099 A1 | 12/2007 | Zahn et al. | |

FOREIGN PATENT DOCUMENTS

| | | | |
|---|---|---|---|
| JP | 50088086 A | * | 7/1975 |
| JP | 2004 186 695 | | 7/2004 |
| JP | 2007 103 558 | | 4/2007 |
| JP | 2007 197 450 | | 8/2007 |
| JP | 2008 007 771 | | 1/2008 |
| JP | 2008 031 430 | | 2/2008 |

OTHER PUBLICATIONS

Mukaiyama et al., CA 84:31061, 1976.*
An English translation of JP 50-088086, 1975.*
Brugier, D. et al. "Alpha-Substitution of Beta-Thienylcarbamates: Alkylation, Vinylation and Pd-Catalyzed Coupling Reactions." Tetrahedron, vol. 56. pp. 2985-2993 (2000).
Galvez, C. et al. "Synthesis of Thiophenedicarbonyldiazides and Di-t-butyl Thiophendicarbamates." Journal of Heterocyclic Chemistry, vol. 23. Pages 1103-1108 (Jul.-Aug. 1986).
International Search Report issued Dec. 15, 2009 in PCT/JP09/067936 filed Oct. 16, 2009.

* cited by examiner

*Primary Examiner* — Laura L. Stockton
(74) *Attorney, Agent, or Firm* — Oblon, Spivak, McClelland, Maier & Neustadt, L.L.P.

(57) ABSTRACT

Provided are a π-electron conjugated polymer having a constitutional unit represented by general formula (2) that is suitable as an electrochromic material that changes from a desired colored state to a decolored state, a new compound that is a raw material of the polymer, and a method for producing the polymer: wherein each X independently represents one selected from the group consisting of an oxygen atom, a sulfur atom, —NH—, and —NR$^1$— (wherein R$^1$ is an optionally substituted alkyl group having 1 to 20 carbon atoms or an optionally substituted aryl group having 6 to 20 carbon atoms); each Y independently represents an oxygen atom or a sulfur atom; each Z independently represents one selected from the group consisting of a hydrogen atom and optionally substituted organic groups having 1 to 20 carbon atoms, and W is one selected from the group consisting of an ethynylene group, an optionally substituted ethenylene group, optionally substituted arylene groups, and optionally substituted divalent heteroaromatic ring groups; and n is an integer of 2 or greater.

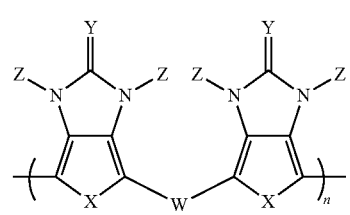

(2)

15 Claims, No Drawings

π-ELECTRON CONJUGATED COMPOUND, MANUFACTURING METHOD THEREFOR, AND π-ELECTRON CONJUGATED POLYMER OBTAINED USING SAME

TECHNICAL FIELD

The present invention relates to a new π-electron conjugated compound, a method for producing the same, and a new π-electron conjugated polymer obtained using the same.

BACKGROUND ART

Recently, the demand for reflective displays that are bright, superior in color purity, and capable of easily performing full-color display with low power consumption has been increasing. For example, conventional light-emission type elements, such as CRTs, LCDs, PDPs and ELDs, have such characteristics that they are bright and easy to see, and therefore a number of technologies have been proposed. However, the above-mentioned light-emission type elements have a problem that they cause visual fatigue when viewed for a long time because emitted light needs to be directly looked at. Moreover, mobile devices such as mobile phones are often used outdoors and there is another problem that emitted light is offset under sunlight, resulting in deterioration in viewability. Meanwhile, among light-emission type elements, especially LCDs are growing in demand and are used for various display applications including large displays and small displays. However, LCDs have a problem that a viewing angle is narrow, and thus they have a problem in terms of viewability that should be improved in comparison to other light-emission type elements.

Meanwhile, although the amount of paper used for storing and conveying documents has been decreasing because of the widespread use of computers in offices, the tendency to print and read digital information in paper is still persistent when such information is perused. Therefore, the amount of paper that is temporally used and abandoned immediately after the use shows an upward trend in recent years, on the contrary. Moreover, the amount of paper that is consumed daily for books, magazines, newspapers and the like is seen as a threat in terms of natural resources and environment, and they do not seem to decrease unless the medium is changed. However, when the way of information recognition and the way of thinking by the human being are taken into consideration, the superiority of "paper" over "display" typified by CRTs (Cathode Ray Tubes: Braun tubes) and transmission type liquid crystal displays cannot be ignored.

Therefore, the electronic paper in which the merit of paper and the merit of displays, which can directly handle digital information, are combined has been recently expected to be put into practical use as an electronic alternative to paper. The characteristics that the electronic paper is required to have include being a reflection type display element, having high reflectivity to white light and high contrast ratio, being capable of displaying with high definition, having a memory effect in display, being capable of driving with a low voltage, being thin and light, being inexpensive, and so on.

The display systems of electronic paper include a reflection type liquid crystal system, an electrophoresis system, a two-color ball system, an electrochromic (hereinafter, sometimes abbreviated as EC) system. Examples of the reflection type liquid crystal system includes a G-H type liquid crystal system using dichromatic pigment, a cholesteric liquid crystal system, and so on. This reflection type liquid crystal system has an advantage that it does not need to use a backlight and thus consumes smaller electrical power in comparison to the existing light-emission type liquid crystal system. However, it involves the dependence on viewing angle and has low light reflectivity, and thereby has a problem that the screen inevitably becomes darker.

The electrophoresis system exploits a phenomenon called "electrophoresis" in which white pigments, black toner, or the like moved onto electrodes by the effect of an electric field. The two-color ball display system involves a spherical body painted with two colors such as white and black in a half-and-half fashion, and uses the rotation by the effect of an electric field. Both the systems have a merit that they consume low electrical power and that they do not involve the dependence on viewing angle. However, it is believed that these systems cannot achieve a high contrast because they require gaps large enough for allowing particulate bodies to enter therein, which makes closest packing difficult. Moreover, when it is to be displayed in full color, a color juxtaposition method using a color filter is adopted, posing a problem that the reflectivity decreases and the screen inevitably becomes darker.

Meanwhile, the EC system is a system in which a reversible oxidation-reduction reaction is caused by an application of an electric field and color development/color disappearance caused by the reaction is exploited. EC display elements have heretofore been used in dimming mirrors of automobiles, clocks, and so on. The display by such an EC display element does not require a polarizing plate and the like, does not involve the dependence on viewing angle, is a light reception type and thus superior in terms of viewability, has a simple structure, and is easily constructed in a large size. Moreover, it has another merit that light emission of various color tones is possible by selecting proper materials.

To show display in full color in an EC display element, there is known a method that uses pigments capable of coloring including cyan (hereinafter, sometimes abbreviated as C), magenta (hereinafter, sometimes abbreviated as M), and yellow (hereinafter, sometimes abbreviated as Y), which are used in subtractive color mixture, and that forms a structure having a C-coloring layer, an M-coloring layer and a Y-coloring layer in a parallel arrangement or in a laminated arrangement. This can afford a display device capable of coloring in full color. For example, black can be displayed by mixing colors of C, M and Y. Moreover, white can be displayed by bringing each pigment to a decolored state while the background color is white. Since the EC display element is a reflection type display element in which coloration/decoloration can be electrically repeated without using a color filter as described above, they are superior to other display systems in terms of burden put on eyes and in terms of contrast.

Research of a material called a π-electron conjugated macromolecule as one of the materials that constitutes the above-mentioned coloring layer has been progressing. There are various π-Electron conjugated polymers including polyacetylene, polypyrrole, polyaniline, polyparaphenylenevinylene, and polythiophene, and they are promising as materials that constitute polymer light-emitting diodes (film displays), solid state lightings, organic photoelectric cells, memory devices, organic field effect transistors, printing electronics, conductors, lasers, sensors, solid capacitors, and so on. Among such π-electron conjugated polymers, polymers exhibiting electrochromic properties are known. It is supposed that in order to obtain an EC element capable of showing colors in full color by the aforementioned coloration/decoloration of C, M, and Y, the electrochromics of a π-electron conjugated macromolecule must change from colored states to colorless states of C, M, and Y, respectively.

However, the electrochromic properties of most of common π-electron conjugated polymers exhibit color change between colored states, and there are a very few materials exhibiting color change from a colored state to a colorless state as described above.

Poly(ethylene-3,4-dioxythiophene) is known as a typical materials which change in color from a colored state to a approximately colorless state. However, this material is a π-electron conjugated macromolecule which changes in color from a navy blue colored state close to C to a pale blue decolored state and no materials which change in color from M or Y to a colorless state have been known.

Patent literature 1 discloses a method for producing a monomer compound such as 1H-thieno[3,4-d]imidazol-2(3H)-one. However, nothing about a monomer compound in which two molecules of 1H-thieno[3,4-d]imidazol-2(3H)-one or the like are linked via an aromatic compound or the like is disclosed and nothing about a polymer to be obtained using the same and the electrochromic properties of this polymer is also disclosed.

Patent literature 2 discloses a polymer having 1H-thieno[3,4-d]imidazol-2(3H)-one or the like as a constitutional unit, and a copolymer having 1H-thieno[3,4-d]imidazol-2(3H)-one or the like and phenylene or the like as constitutional units. However, nothing about a monomer compound in which two molecules of 1H-thieno[3,4-d]imidazol-2(3H)-one or the like are linked via an aromatic compound or the like is disclosed and nothing about a polymer to be obtained using the same is also disclosed.

PRIOR ART DOCUMENTS

Patent Documents

Patent document 1: JP 2008-7771 A
Patent document 2: JP 2008-31430 A

SUMMARY OF THE INVENTION

Problems to be Solved by the Invention

In order to solve the above-mentioned problems, an objective of the present invention is to provide a novel polymer that is suitable as an electrochromic material that transfers from a desired colored state to a decolored state, a novel compound that is a raw material of the foregoing polymer, and a method for producing the polymer.

Means for Solving the Problems

The above-mentioned problems are solved by providing a π-electron conjugated compound represented by general formula (1):

[Chem. 1]

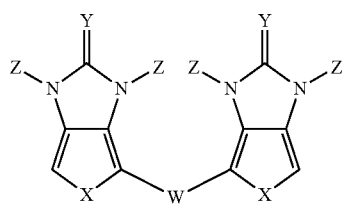

(1)

wherein each X independently represents one selected from the group consisting of an oxygen atom, a sulfur atom, —NH—, and —NR$^1$— (wherein R$^1$ is an optionally substituted alkyl group having 1 to 20 carbon atoms or an optionally substituted aryl group having 6 to 20 carbon atoms); each Y independently represents an oxygen atom or a sulfur atom; each Z independently represents one selected from the group consisting of a hydrogen atom and optionally substituted organic groups having 1 to 20 carbon atoms, and W is one selected from the group consisting of an ethynylene group, an optionally substituted ethenylene group, optionally substituted arylene groups, and optionally substituted divalent heteroaromatic ring groups.

Moreover, the above-mentioned problems are solved also by providing a π-electron conjugated compound having a constitutional unit represented by general formula (2):

[Chem. 2]

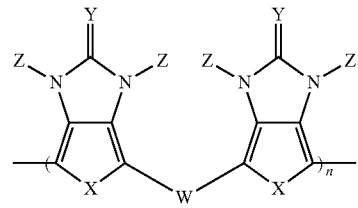

(2)

wherein each X independently represents one selected from the group consisting of an oxygen atom, a sulfur atom, —NH—, and —NR$^1$— (wherein R$^1$ is an optionally substituted alkyl group having 1 to 20 carbon atoms or an optionally substituted aryl group having 6 to 20 carbon atoms); each Y independently represents an oxygen atom or a sulfur atom; each Z independently represents one selected from the group consisting of a hydrogen atom and optionally substituted organic groups having 1 to 20 carbon atoms, and W is one selected from the group consisting of an ethynylene group, an optionally substituted ethenylene group, optionally substituted arylene groups, and optionally substituted divalent heteroaromatic ring groups; and n is an integer of 2 or greater.

At this time, a preferred embodiment of the present invention is an electrochromic material composed of a π-electron conjugated polymer represented by general formula (2). Another preferred embodiment of the present invention is a method for producing a π-electron conjugated compound, comprising:
halogenating a compound represented by general formula (3):

[Chem. 3]

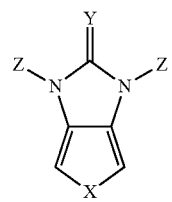

(3)

wherein X, Y, and Z are as defined above to obtain a compound represented by general formula (4):

[Chem. 4]

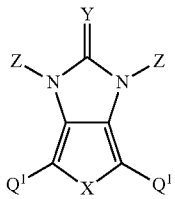

(4)

wherein X, Y, and Z are as defined above and each $Q^1$ independently represents a halogen atom;

subsequently lithiating the compound thus obtained, to which an acid is then added to obtain a compound represented by general formula (5):

[Chem. 5]

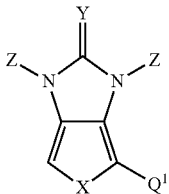

(5)

wherein X, Y, Z, and $Q^1$ are as defined above; and then cross-coupling the compound thus obtained with a compound represented by general formula (6):

[Chem. 6]

$Q^2$-W-$Q^2$ (6)

wherein W is as defined above, $Q^2$ is one selected from the group consisting of —MgCl, —MgBr, —MgI, —ZnCl, —ZnBr, —ZnI, —Sn($R^2$)$_3$ (wherein each $R^2$ independently represents an optionally substituted alkyl group having 1 to 20 carbon atoms or an optionally substituted alkoxy group having 1 to 20 carbon atoms), a boronic acid group, and a boronic acid ester group.

In addition, at this time, another preferred embodiment of the present invention is a method for producing a π-electron conjugated compound, comprising:

reacting a compound represented by general formula (3):

[Chem. 7]

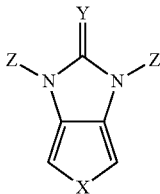

(3)

wherein X and Y are as defined above and each Z independently represents an optionally substituted organic group having 1 to 20 carbon atoms with one selected from the group consisting of MgCl$_2$, MgBr$_2$, MgI$_2$, ZnCl$_2$, ZnBr$_2$, ZnI$_2$, Sn($R^2$)$_3$C (wherein each $R^2$ independently represents an optionally substituted alkyl group having 1 to 20 carbon atoms or an optionally substituted alkoxy group having 1 to 20 carbon atoms), Sn($R^2$)$_3$Br, Sn($R^2$)$_3$I, boronic acid, and a boronic acid ester in the presence of a base, to obtain a compound represented by general formula (7):

[Chem. 8]

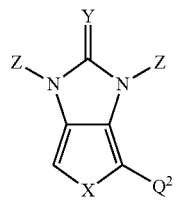

(7)

wherein X, Y, and Z are as defined above, $Q^2$ is one selected from the group consisting of —MgCl, —MgBr, —MgI, —ZnCl, —ZnBr, —ZnI, —Sn($R^2$)$_3$ (wherein each $R^2$ independently represents an optionally substituted alkyl group having 1 to 20 carbon atoms or an optionally substituted alkoxy group having 1 to 20 carbon atoms), a boronic acid group, and a boronic acid ester group; and then cross-coupling the compound thus obtained with a compound represented by general formula (8):

[Chem. 9]

$Q^1$-W-$Q^1$ (8)

wherein W is as defined above and each $Q^1$ independently represents a halogen atom.

A preferred embodiment of the present invention is a method for producing a π-electron conjugated compound, comprising:

reacting a compound represented by general formula (9):

[Chem. 10]

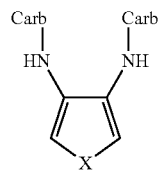

(9)

wherein X is as defined above, each Carb independently represents an organic oxycarbonyl group or an organic oxythiocarbonyl group with a basic substance; and then further reacting the reaction product with at least one compound selected from the group consisting of magnesium compounds, zinc compounds, tin compounds, boron compounds, and halogens to obtain a compound represented by general formula (10):

[Chem. 11]

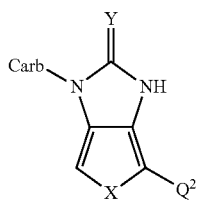

(10)

wherein X, Y, and Carb are as defined above, and $Q^2$ is one selected from the group consisting of —MgCl, —MgBr, —MgI, —ZnCl, —ZnBr, —ZnI, —Sn($R^2$)$_3$ (wherein each $R^2$ independently represents an optionally substituted alkyl group having 1 to 20 carbon atoms or an optionally substituted alkoxy group having 1 to 20 carbon atoms), a boronic acid group, and a boronic acid ester group, or an anionic compound having a structure resulting from the removal of an active proton from the compound represented by general formula (10).

A preferred embodiment of the present invention is a method for producing a π-electron conjugated compound, further comprising reacting a compound represented by general formula (9):

[Chem. 12]

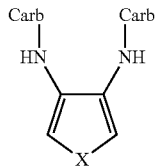

(9)

wherein X is as defined above and each Carb independently represents an organic oxycarbonyl group or an organic oxythiocarbonyl group with a basic compound; and then further reacting the reaction product react with at least one compound selected from the group consisting of magnesium compounds, zinc compounds, tin compounds, boron compounds, and halogens to obtain a compound represented by general formula (13):

[Chem. 13]

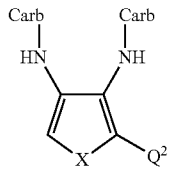

(13)

wherein X and Carb are as defined above, and $Q^2$ is one selected from the group consisting of —MgCl, —MgBr, —MgI, —ZnCl, —ZnBr, —ZnI, —Sn($R^2$)$_3$ (wherein each $R^2$ independently represents an optionally substituted alkyl group having 1 to 20 carbon atoms or an optionally substituted alkoxy group having 1 to 20 carbon atoms), a boronic acid group, and a boronic acid ester group, or an anionic compound having a structure resulting from the removal of an active proton from the compound represented by general formula (7).

Moreover, the aforementioned problems are solved also by providing a compound represented by general formula (10):

[Chem. 14]

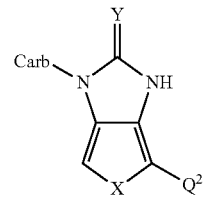

(10)

wherein X is selected from the group consisting of an oxygen atom, a sulfur atom, —NH—, and —$NR^1$— (wherein $R^1$ is an optionally substituted alkyl group having 1 to 20 carbon atoms or an optionally substituted aryl group having 6 to 20 carbon atoms); Y is an oxygen atom or a sulfur atom; Carb is an organic oxycarbonyl group or an organic oxythiocarbonyl group; and $Q^2$ is selected from the group consisting of —MgCl, —MgBr, —MgI, —ZnCl, —ZnBr, —ZnI, —Sn ($R^2$)$_3$ (wherein each $R^2$ independently represents an optionally substituted alkyl group having 1 to 20 carbon atoms or an optionally substituted alkoxy group having 1 to 20 carbon atoms), a boronic acid group, and a boronic acid ester group, or an anionic compound having a structure resulting from the removal of an active proton from the compound represented by general formula (10).

Effects of the Invention

According to the present invention, a novel compound, a method for producing the same, and a new polymer to be obtained using the same can be provided. A new polymer obtained in this way has a characteristic that it changes from a colored state at the time of undoping to a decolored state in which the polymer has no absorption maximum in a visible range at the time of doping. Therefore, it can be suitably used as an electrochromic material that changes from a desired colored state to a decolored state.

MODE FOR CARRYING OUT THE INVENTION

According to the present invention, there can be provided a π-electron conjugated compound represented by general formula (1) and a π-electron conjugated polymer having a constitutional unit represented by general formula (2) to be obtained using the foregoing compound. All of these compounds are novel compounds. Details are described below.

[Chem. 15]

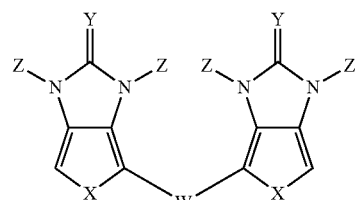

(1)

wherein each X independently represents one selected from the group consisting of an oxygen atom, a sulfur atom, —NH—, and —NR$^1$— (wherein R$^1$ is an optionally substituted alkyl group having 1 to 20 carbon atoms or an optionally substituted aryl group having 6 to 20 carbon atoms); each Y independently represents an oxygen atom or a sulfur atom; each Z independently represents one selected from the group consisting of a hydrogen atom and optionally substituted organic groups having 1 to 20 carbon atoms, and W is one selected from the group consisting of an ethynylene group, an optionally substituted ethenylene group, optionally substituted arylene groups, and optionally substituted divalent heteroaromatic ring groups.

[Chem. 16]

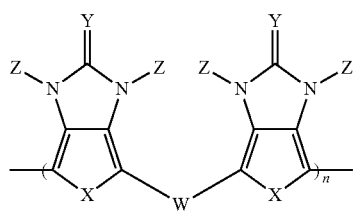

(2)

wherein X, Y, Z, and W are as defined in general formula (1), and n is an integer of 2 or greater.

In general formulas (1) and (2), each X independently represents one selected from the group consisting of an oxygen atom, a sulfur atom, —NH—, and —NR$^1$— (R$^1$ is an optionally substituted alkyl group having 1 to 20 carbon atoms or an optionally substituted aryl group having 6 to 20 carbon atoms); each Y independently represents an oxygen atom or a sulfur atom; each Z independently is one selected from the group consisting of a hydrogen atom and optionally substituted organic groups having 1 to 20 carbon atoms, and W is one selected from the group consisting of an ethynylene group, an optionally substituted ethenylene group, optionally substituted arylene groups, and optionally substituted divalent heteroaromatic ring groups.

R$^1$ in —NR$^1$— in X is an optionally substituted alkyl group having 1 to 20 carbon atoms or an optionally substituted aryl group having 6 to 20 carbon atoms. The optionally substituted alkyl group having 1 to 20 carbon atoms may be either a straight chain or a branched chain. Specific examples of the alkyl group having 1 to 20 carbon atoms include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, an isohexyl group, a 2-ethylhexyl group, a n-heptyl group, a n-octyl group, a n-nonyl group, and a n-decyl group. Examples of the aryl group having 6 to 20 carbon atoms include a phenyl group, a naphthyl group, an anthryl group, and a phenanthryl group. Among these, R$^1$ is preferably an optionally substituted alkyl group having 1 to 20 carbon atoms, more preferably an optionally substituted alkyl group having 1 to 10 carbon atoms.

In general formulas (1) and (2), X is preferably an oxygen atom or a sulfur atom and it is more preferably a sulfur atom from the viewpoints of availability of a raw material and ease in a production method.

In addition, in general formulas (1) and (2), each Y independently is an oxygen atom or a sulfur atom, and two Ys may be either the same or different. In general formula (1), Y is preferably an oxygen atom from the viewpoints of availability of a raw material, ease in synthesis and production in a high yield.

In general formulas (1) and (2), each Z independently is one selected from the group consisting of a hydrogen atom and optionally substituted organic groups having 1 to 20 carbon atoms. A plurality of Zs may be either the same or different. The optionally substituted organic groups having 1 to 20 carbon atoms may contain in their structure a bond other than a carbon-carbon bond, such as an ether bond, an ester bond, an amide bond, a sulfonyl bond, a urethane bond and a thioether bond and also may contain a double bond, a triple bond, an alicyclic hydrocarbon, a heterocycle, an aromatic hydrocarbon, a heteroaromatic ring, and so on. Furthermore, it also may have a substituent, such as a halogen atom, a hydroxyl group, an amino group, a cyano group, and a nitro group. Examples of the optionally substituted organic groups having 1 to 20 carbon atoms include optionally substituted alkyl groups having 1 to 20 carbon atoms, optionally substituted alkenyl groups having 2 to 20 carbon atoms, optionally substituted aryl groups having 6 to 20 carbon atoms, optionally substituted cycloalkyl groups having 3 to 20 carbon atoms, optionally substituted cycloalkenyl groups having 3 to 20 carbon atoms, optionally substituted alkoxy groups having 1 to 20 carbon atoms, optionally substituted acyl groups having 2 to 20 carbon atoms, optionally substituted arylalkyl groups having 7 to 20 carbon atoms, optionally substituted alkylsilyl groups having 3 to 20 carbon atoms, optionally substituted alkoxycarbonyl groups having 2 to 20 carbon atoms, and optionally substituted heteroaromatic ring groups having 1 to 20 carbon atoms.

The alkyl groups having 1 to 20 carbon atoms provided as examples in the description of the above-described R$^1$ can be used as the alkyl groups having 1 to 20 carbon atoms.

Examples of the alkenyl groups having 2 to 20 carbon atoms include a vinyl group, an allyl group, a methylvinyl group, a propenyl group, a butenyl group, a pentenyl group, and a hexenyl group.

Examples of the aryl groups having 6 to 20 carbon atoms include a phenyl group, a naphthyl group, an anthryl group, and a phenanthryl group.

Examples of the cycloalkyl groups having 3 to 20 carbon atoms include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

Examples of the cycloalkenyl groups having 3 to 20 carbon atoms include a cyclopropenyl group, a cyclobutenyl group, a cyclopentenyl group, and a cyclohexenyl group.

Examples of the alkoxy groups having 1 to 20 carbon atoms include a methoxy group, an ethoxy group, a n-propoxy, an isopropoxy group, a n-butoxy group, an isobutoxy group, a sec-butoxy group, a tert-butoxy group, a n-pentyloxy group, an isopentyloxy group, a neopentyloxy group, a n-hexyloxy group, an isohexyloxy group, a 2-ethylhexyloxy group, a n-heptyloxy group, a n-octyloxy group, a n-nonyloxy group, and a n-decyloxy group.

Examples of the acyl groups having 2 to 20 carbon atoms include an acetyl group, a propionyl group, a butyryl group, an isobutyryl group, a benzoyl group, a dodecanoyl group, and a pivaloyl group.

Examples of the arylalkyl groups having 7 to 20 carbon atoms include a benzyl group, a 4-methoxybenzyl group, a phenethyl group, and a diphenylmethyl group.

Examples of the alkyl silyl groups having 3 to 20 carbon atoms include a trimethylsilyl group, a triethyl silyl group, a triisopropyl silyl group, a tert-butyldimethylsilyl group, and a tert-butylphenylsilyl group.

Examples of the alkoxycarbonyl groups having 2 to 20 carbon atoms include a methoxycarbonyl group, an ethoxy-carbonyl group, a 2,2,2-trichloroethoxycarbonyl group, a n-propoxycarbonyl group, an isopropoxycarbonyl group, an allyloxy carbonyl group, a n-butoxycarbonyl group, an iso-carbobutoxy group, a sec-butoxycarbonyl group, a tert-butoxycarbonyl group, a pentyloxycarbonyl group, a hexyloxycarbonyl group, a heptyloxycarbonyl group, an octyloxycarbonyl group, and a benzyloxycarbonyl group.

Examples of the heteroaromatic ring groups having 1 to 20 carbon atoms include a thienyl group, a furyl group, a pyridyl group, an imidazolyl group, a pyrazinyl group, an oxazolyl group, an thiazolyl group, a pyrazolyl group, a benzothiazolyl group, and a benzimidazolyl group.

Among these, Z is preferably a hydrogen atom or an optionally substituted alkyl group having 1 to 20 carbon atoms, and particularly when Z is a hydrogen atom, it is desirable because a π-electron conjugated polymer represented by general formula (2) to be obtained using the compound represented by general formula (1) as a monomer component improves in planarity and in stacking between molecular chains due to intramolecular and intermolecular chain interaction via hydrogen bonding, exhibiting excellent transparency in a decolored state. It is preferred that all Zs be the same.

W is one selected from the group consisting of an ethynylene group, an optionally substituted ethenylene group, an optionally substituted arylene group and an optionally substituted divalent heteroaromatic group.

The ethynylene group is a divalent group that has a structure resulting from removing two hydrogen atoms from acetylene ($C_2H_2$), and examples of the optionally substituted ethenylene group include a group represented by —CH=CH—.

Examples of the optionally substituted arylene groups include a phenylene group, a 2,3-dialkylphenylene group, a 2,5-dialkylphenylene group, a 2,3,5,6-tetraalkylphenylene group, a 2,3-alkoxyphenylene group, a 2,5-alkoxyphenylene group, 2,3,5,6-tetraalkoxyphenylene group, a 2-(N,N-dialkylamino)phenylene group, a 2,5-di(N,N-dialkylamino)phenylene group, a 2,3-di(N,N-dialkylamino)phenylene group, a p-phenyleneoxy group, a p-phenylenesulfide group, a p-phenyleneamino group, a p-phenylenevinylene group, a fluorenylene group, a naphthylene group, an anthrylene group, a tetracenylene group, a pentacenylene group, a hexacenylene group, a heptacenylene group, a naphthylenevinylene group, a perinaphthylene group, an aminopyrenylene group, and a phenanthrenylene group, and one selected from these is suitably used.

Examples of the divalent heteroaromatic ring groups include carbazole derivatives, such as N-alkylcarbazole; pyridine derivatives, such as pyrimidine, pyridazine, triazine, pyrazine, quinoline, and purine; furan derivatives, such as 3-alkylfuran; pyrrole derivatives, such as N-alkylpyrrole, ethylene-3,4-dioxypyrrole, and propylene-3,4-dioxypyrrole; thiophene derivatives, such as thiophenevinylene, alkylthiophene, ethylene-3,4-dioxythiophene, propylene-3,4-dioxythiophene, thienothiophene, thienofuran, thienopyrazine, and isothianaphthene; heterocyclic ring derivatives, such as oxadiazole, thiazyl, selenophene, tellurophene, imidazole, oxazole, thiazole, pyrazole, isoxazole, isothiazole, benzotriazole, pyrane, benzothiadiazole, and benzoxadiazole, and one selected from these is suitably used.

Among these, W is preferably an optionally substituted arylene group or an optionally substituted divalent heteroaromatic ring group.

Examples of the substituents in the descriptions of the above-described $R^1$, Z and W and the descriptions of the Carb and $R^2$ described later include, but not limited to, oxy groups, such as alkoxy groups; oxycarbonyl groups, such as alkoxycarbonyl groups; carbonyloxy groups, such as alkylcarbonyloxy groups; aminocarbonyl groups, such as alkylaminocarbonyl groups; carbonylamino groups, such as alkylcarbonylamino groups; sulfonyl groups, such as alkylsulfonyl groups; oxycarbonylamino groups, such as alkyloxycarbonylamino groups; aminocarbonyloxy groups, such as alkylaminocarbonyloxy groups; thio groups, such as alkylthio groups; alkyl groups; alkenyl groups; alkynyl groups; cycloalkyl groups; aryl groups; heterocyclic groups, such as heteroaromatic ring groups; halogen atoms; a hydroxyl group; an amino group; a cyano group; and a nitro group. Although the number of the substituent is not particularly limited, it is preferably from 0 to 5, more preferably from 0 to 3, and even more preferably from 0 to 1. The number of the substituent may be 0 (zero). The number of carbon atoms in the substituent (the total carbon number when $R^1$, Z, W, Carb, or $R^2$ has two or more substituents) is preferably within the range of from 0 to 20, more preferably within the range of from 0 to 10.

In the present invention, the π-electron conjugated compound represented by general formula (1) is preferably synthesized from a compound represented by general formula (3) as in reactions 1 to 3 shown by chemical reaction formula (I) (First production method).

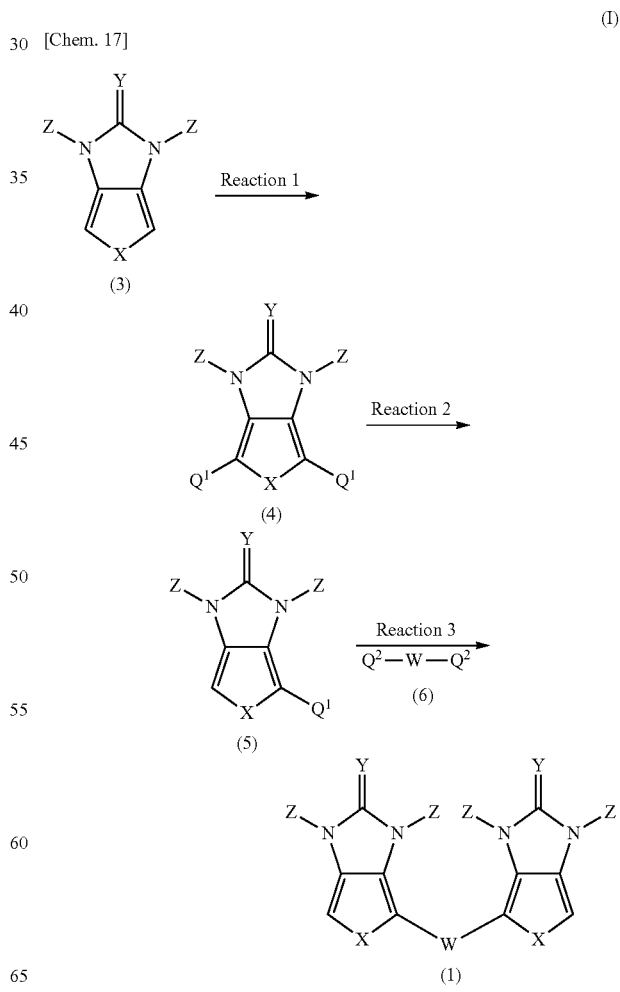

wherein X, Y, Z and W are as defined above, $Q^1$ is a halogen atom, and $Q^2$ is one selected from the group consisting of —MgCl, —MgBr, —MgI, —ZnCl, —ZnBr, ZnI, —Sn($R^2$)$_3$ (wherein each $R^2$ independently is an optionally substituted alkyl group having 1 to 20 carbon atoms or an optionally substituted alkoxy group having 1 to 20 carbon atoms), a boronic acid group, and a boronic acid ester group.

$Q^1$ in each of the compounds represented by general formulas (4) and (5) is a halogen atom, and examples of the halogen atom include fluorine, chlorine, bromine, and iodine. Although $Q^2$ in the compound represented by general formula (6) is one selected from the group consisting of —MgCl, —MgBr, —MgI, —ZnCl, —ZnBr, ZnI, —Sn($R^2$)$_3$ (wherein each $R^2$ independently is an optionally substituted alkyl group having 1 to 20 carbon atoms or an optionally substituted alkoxy group having 1 to 20 carbon atoms), a boronic acid group, and a boronic acid ester group, —Sn($R^2$)$_3$ is preferably used from, for example, the viewpoints that the reaction proceeds under an approximately neutral reaction condition and that the reaction has large functional group tolerance. Each $R^2$ independently represents an optionally substituted alkyl group having 1 to 20 carbon atoms or an optionally substituted alkoxy group having 1 to 20 carbon atoms; the alkyl groups provided as examples in the description of the above-described $R^1$ can be used as the alkyl group, and the alkoxy groups provided as examples in the description of the above-described Z can be used as the alkoxy group. Suitable $R^2$ is an optionally substituted alkyl group having 1 to 10 carbon atoms or an optionally substituted alkoxy group having 1 to 10 carbon atoms.

Reactions 1 and 2 in chemical reaction formula (I) are reactions in which a compound represented by general formula (4) is obtained through the introduction of halogen atoms to the two α-positions to the X in a compound represented by general formula (3) and then a compound represented by general formula (5) having a halogen atom introduced to one α-position to the X is obtained through lithiation and addition of an acid. In a case where at least one of the Zs in the compound represented by general formula (3) is a hydrogen atom, if a halogen atom is introduced after removing the hydrogen of the α-position to the X using a base, a side reaction in which a hydrogen atom in the Zs is preferentially removed may occur. Therefore, a halogen atom is suitably introduced by a radical reaction involving, for example, N-bromosuccinimide. Even if the amount of a radical reaction reagent, such as N-bromosuccinimide, is adjusted when introducing a halogen atom to be a required amount, two products, i.e., a product in which halogen atoms have been introduced to two α-positions to X simultaneously and a product in which no halogen atoms have been introduced, are obtained, so that a separation-purification step may be required, leading to a complicated process. Therefore, a process of Reaction 1 for obtaining a compound represented by general formula (4) and then Reaction 2 for lithiating a halogen atom and stopping the reaction by a proton is preferred because a compound represented by general formula (5) can be obtained in a high yield.

It is preferred that reactions 1 and 2 be carried out in the presence of a solvent. Examples of such a solvent include saturated aliphatic hydrocarbons, such as pentane, hexane, heptane, octane, nonane, decane, and cyclohexane; aromatic hydrocarbons, such as benzene, toluene, ethylbenzene, propylbenzene, xylene, and ethyltoluene; ethers, such as dimethyl ether, ethyl methyl ether, diethyl ether, dipropyl ether, butyl methyl ether, tert-butyl methyl ether, dibutyl ether, tetrahydrofuran, and 1,4-dioxane; aprotic polar solvents, such as dimethylacetamide, dimethylformamide, N-methyl-2-pyrrolidone, and dimethyl sulfoxide. Among these, ethers are preferably used, and specifically, the use of diethyl ether or tetrahydrofuran is preferred. The solvents may be used alone or in combination of two or more. The amount of such a solvent is preferably from 1 to 100 ml, more preferably from 2 to 20 ml relative to 1 mmol of the compound represented by general formula (3).

Reaction 2 is a reaction in which a compound represented by general formula (5) is obtained by lithiating the compound represented by general formula (4) and then adding an acid. In the lithiation, an organolithium compound is preferably used. Specific examples of an organolithium compound to be used include alkyllithium compounds, such as methyllithium, n-butyllithium, sec-butyllithium, and tert-butyllithium; aryllithium compounds, such as phenyllithium; alkenyllithium compounds, such as vinyllithium; and lithium amide compounds, such as lithium diisopropylamide and lithium bistrimethylsilylamide. Among these, it is preferred to use an alkyllithium compound. The amount of an organolithium compound is not particularly limited and it is preferably from 0.5 to 5 mol relative to 1 mol of the compound represented by general formula (4). When the amount of the organolithium compound exceeds 5 mol, a side reaction or the decomposition of a product may be promoted, and it is more preferred to be 4 mol or less. It is more preferred that the amount of the organolithium compound be not less than 1 mol.

The reaction temperature at which the lithiation is carried out is not particularly limited, and it is preferred to be within a range of from −100 to 25° C. When the reaction temperature is lower than −100° C., the rate of reaction may become very slow, and it is more preferred to be not lower than −90° C. On the other hand, when the reaction temperature exceeds 25° C., there is a possibility of promoting the decomposition of a product or promoting a side reaction, and it is more preferred to be not higher than 20° C. The reaction time is preferred to be from 1 minute to 10 hours, more preferred to be from 5 minutes to 5 hours. The acid to be used in reaction 2 is not particularly restricted, and besides acids such as hydrochloric acid and sulfuric acid, protonic polar solvents, such as water, methanol, and ethanol, are suitably used.

Subsequently, a π-electron conjugated compound represented by general formula (1) can be obtained by cross-coupling a compound represented by general formula (5) with a compound represented by general formula (6) as shown by reaction 3. For example, a Suzuki reaction, a Yamamoto reaction, a Heck reaction, a Stille reaction, a Sonogashira-Hagihara reaction, a Kumada-Corriu reaction, a Rieeke reaction, a McCullog reaction, and so on are adopted suitably as the cross-coupling reaction.

In the present invention, the π-electron conjugated compound represented by general formula (1) can be synthesized also from a compound represented by general formula (3) via reactions 4 and 5 shown by chemical reaction formula (II) (second production method).

[Chem. 18]

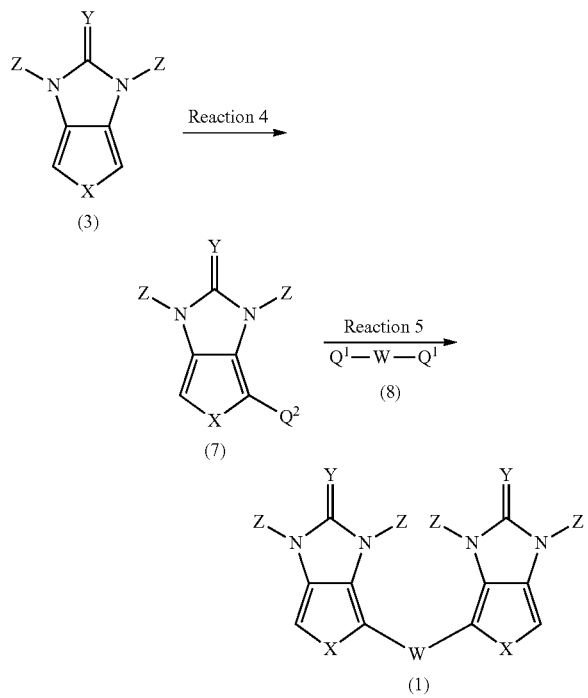

wherein X, Y, W, $Q^1$, and $Q^2$ are as defined above and each Z independently is an optionally substituted organic group having 1 to 20 carbon atoms.

Reaction 4 is a reaction of obtaining a compound represented by general formula (7) by reacting a compound represented by general formula (3) with at least one selected from the group consisting of $MgCl_2$, $MgBr_2$, $MgI_2$, $ZnCl_2$, $ZnBr_2$, $ZnI_2$, $Sn(R^2)_3Cl$ (wherein each $R^2$ independently is an optionally substituted alkyl or alkoxy group having 1 to 20 carbon atoms), $Sn(R^2)_3Br$, $Sn(R^2)_3I$, boronic acid, and a boronic acid ester in the presence of a base. The base to be used in reaction 4 is not particularly restricted, and an organolithium compound is suitably used. The compounds provided as examples in the description of reaction 2 can be used as the organolithium compound.

In reaction 4, when at least one of the Zs is a hydrogen atom, a side reaction in which a hydrogen atom of the Zs is preferentially removed may occur during introducing a substituent $Q^2$ by removing the hydrogen of the α-position to the X using a base. Therefore, it is preferred in reaction 4 that the Zs in the compound represented by general formula (3) are independently of each other an optionally substituted organic group having 1 to 20 carbon atoms. The groups provided as examples in the description of general formulas (1) and (2) described above can be used as the optionally substituted organic group having 1 to 20 carbon atoms.

In chemical reaction formula (II) shown above, it is also permissible to carry out a reaction of replacing Z with a hydrogen atom after the substituent $Q^2$ is introduced by reaction 4. This is preferred because this can enhance hydrogen-bond forming ability of a resulting compound represented by general formula (1).

The compound represented by general formula (1) can be obtained by cross-coupling the compound represented by general formula (7) obtained by reaction 4 with a compound represented by general formula (8). The reactions provided as examples in the description of above-described reaction 3 can be adopted as the cross-coupling reaction.

The compound represented by general formula (3) to be used in the present invention can be synthesized using a compound represented by general formula (15) as a starting compound:

[Chem. 19]

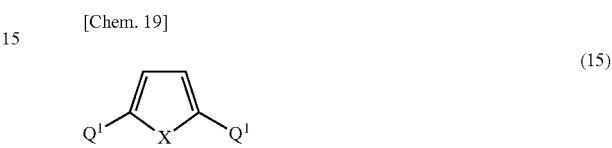

wherein X is one selected from the group consisting of an oxygen atom, a sulfur atom, —NH—, and —$NR^1$— (wherein $R^1$ is an optionally substituted alkyl group having 1 to 20 carbon atoms or an optionally substituted aryl group having 6 to 20 carbon atoms), and $Q^1$ is a halogen atom.

There will be described a method for obtaining 1H-thieno[3,4-d]imidazol-2(3H)-one represented by formula (3a), which is a compound represented by general formula (3) wherein X is a sulfur atom, Y is an oxygen atom, and each Z is a hydrogen atom, by using 2,5-dibromothiophene represented by formula (15a), which is a compound represented by general formula (15) wherein X is a sulfur atom and each $Q^1$ is Br, as a starting compound with reference to chemical reaction formula (III).

[Chem. 20]

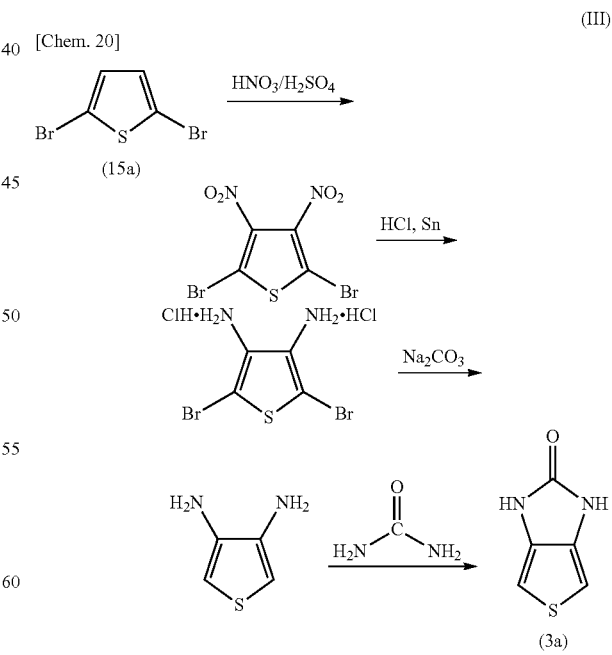

As shown in chemical reaction formula (III), first, a preferred reaction is carried out, where a solution of 2,5-dibromothiophene represented by formula (15a) in concentrated sulfuric acid is added to mixed acid (fuming nitric acid and fuming sulfuric acid) to obtain 2,5-dibromo-3,4-dinitrothiophene nitrated at 3-position and 4-position, and then 3,4-diaminothiophene dihydrochloride, which is a hydrochloride, is obtained using hydrochloric acid and tin (Sn). Further, the resulting hydrochloride is treated with a base such as sodium carbonate, to obtain 3,4-diaminothiophene, which can be then reacted with urea, to give 1H-thieno[3,4-d]imidazol-2(3H)-one represented by formula (3a).

In the present invention, a π-electron conjugated compound represented by general formula (12) that is one preferred embodiment of the π-electron conjugated compound represented by general formula (1) is preferably synthesized from a compound represented by general formula (9) as in reactions A to C shown by chemical reaction formula (IV) (third production method).

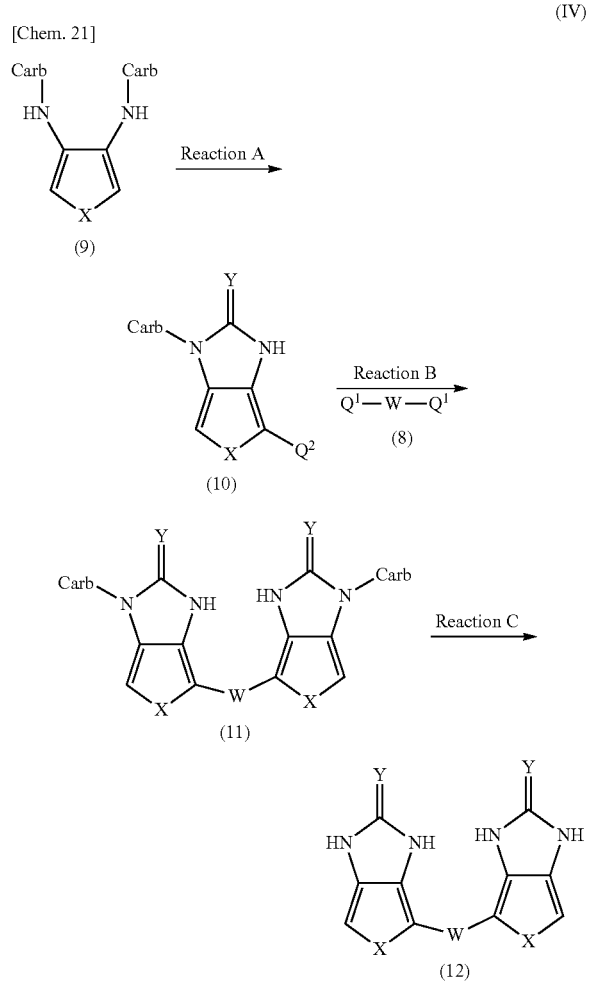

wherein X, Y, W, $Q^1$, and $Q^2$ are as defined above, and each Carb independently is an organic oxycarbonyl group or an organic oxythiocarbonyl group.

In the production method of the present invention, a compound represented by general formula (9) is used as a raw material.

[Chem. 22]

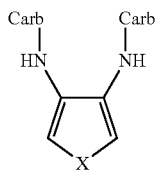

wherein X is as defined above, and each Carb independently is an organic oxycarbonyl group or an organic oxythiocarbonyl group.

The X in general formula (9) should be the same as the X in general formula (1) depending upon a desired compound represented by general formula (1).

Moreover, depends on the kind of the target product, the Carb in general formula (9) shown above is preferably, from the viewpoints of the reactivity of the compound represented by general formula (9), the stability in a reaction, the ease in removal, and so on, selected from the group consisting of optionally substituted alkyloxycarbonyl groups having 2 to 20 carbon atoms, optionally substituted alkenyloxycarbonyl groups having 3 to 20 carbon atoms, optionally substituted cycloalkyloxycarbonyl groups having 7 to 20 carbon atoms, optionally substituted aryloxycarbonyl groups having 7 to 20 carbon atoms, optionally substituted aralkyloxycarbonyl groups having 8 to 20 carbon atoms, and optionally substituted alkylaryloxycarbonyl groups having 8 to 20 carbon atoms, and it is more preferably selected from a tert-butoxycarbonyl group (hereinafter, sometimes abbreviated as Boc), a 2,2,2-trichloroethoxycarbonyl group (hereinafter, sometimes abbreviated as Troc), an allyloxycarbonyl group (hereinafter, sometimes abbreviated as Alloc), a benzyloxycarbonyl group (hereinafter, sometimes abbreviated as Cbz), and a 9-fluorenylmethyloxycarbonyl group (hereinafter, sometimes abbreviated as Fmoc).

In general formula (9) shown above, although the two Carb's may be identical or different from each other, it is preferred that they be identical from the viewpoint of, for example, the ease of preparing the compound represented by general formula (9).

The method for preparing the compound represented by general formula (9) shown above is not particularly restricted, and it can be produced by, for example, reacting a carbamate-forming compound, such as di-tert-butyl dicarbonate, diallyl dicarbonate, dibenzyl dicarbonate, methyl chloroformate, ethyl chloroformate, benzyl chloroformate, 4-nitrophenyl chloroformate, 2,2,2-trichloroethyl chloroformate, 9-fluorenylmethyl chloroformate, 2-(tert-butoxycarbonylthio)-4,6-dimethylpyrimidine, N-tert-butoxycarbonylimidazole, 2-(tert-buthoxycarbonyloxyimino)-2-phenylacetonitrile, 1-tert-carbobutoxy-1,2,4-triazole, carbonic acid tert-butyl phthalimido ester, carbonic acid tert-butyl 2,4,5-trichlorophenyl ester, dibenzyl carbonate, and N-carboethoxyphthalimide, with corresponding 3,4-diaminofuran, 3,4-diaminothiophen, or an N-substituted or unsubstituted 3,4-diaminopyrrole.

The third production method of the present invention includes the step of reacting the compound represented by general formula (9) shown above with a basic substance, and then further reacting the reaction product with at least one compound selected from the group consisting of magnesium compounds, zinc compounds, tin compounds, boron compounds, and halogens, to give a compound represented by general formula (10) or an anion compound having a structure resulting from the removal of an active proton from that compound.

[Chem. 23]

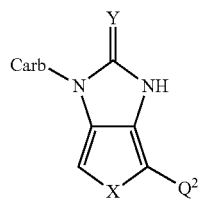

(10)

In general formula (10) shown above, X, Y, and Carb are as defined above, and $Q^2$ is selected from the group consisting of —MgCl, —MgBr, —MgI, —ZnCl, —ZnBr, —ZnI, —Sn$(R^2)_3$, a boronic acid group, and a boronic acid ester group. Each $R^2$ in —Sn$(R^2)_3$ that is represented by $Q^2$ in general formula (10) shown above is independently an optionally substituted alkyl group having 1 to 20 carbon atoms (preferably, 1 to 10 carbon atoms) or an optionally substituted alkoxy group having 1 to 20 carbon atoms (preferably, 1 to 10 carbon atoms), and the plurality of $R^2$'s may be the same or different from each other.

Examples of the alkyl group having 1 to 20 carbon atoms include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, an isohexyl group, a 2-ethylhexyl group, a n-heptyl group, a n-octyl group, a n-nonyl group, and a n-decyl group. Examples of the alkoxy groups having 1 to 20 carbon atoms include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a neopentyloxy group, a n-hexyloxy group, an isohexyloxy group, a 2-ethylhexyloxy group, a n-heptyloxy group, a n-octyloxy group, a n-nonyloxy group, and a n-decyloxy group. It is preferred that the $Q^2$ in general formula (10) shown above be —Sn$(R^2)_3$ because a subsequent reaction can be carried out under an approximately neutral condition.

Specific examples of the anion compound having a structure resulting from the removal of an active proton from the compound represented by general formula (10) include an anion compound represented by general formula (10') or its tautomer or a compound in which an anion existing on a nitrogen atom in general formula (10') is delocalized together with a neighbouring π-electron.

[Chem. 24]

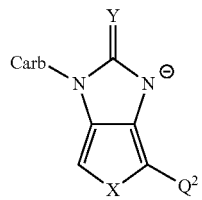

(10')

wherein X, Y, Carb, and $Q^2$ are as defined above.

The counter cation to the anion compound depends on the kind of the basic substance to be used and so on, and examples thereof include cations of alkali metals, such as lithium ion, sodium ion, and potassium ion; cations of alkaline earth metals, such as magnesium ion and calcium ion; and ammonium ion. Such an anion compound is preferred when $Q^2$ is selected from the group consisting of —MgCl, —MgBr, —MgI, —ZnCl, —ZnBr, and —ZnI.

Moreover, the compound represented by general formula (10) and the anionic compound having a structure resulting from the removal of an active proton from that compound are novel compounds that are useful as synthetic intermediates in producing the compound represented by general formula (1), and the present invention encompasses these compounds.

Although a compound capable of affording a compound that serves as a precursor of a compound represented by general formula (10) by reacting with a compound represented by general formula (9) can be used as the basic substance to be used in the present invention, the basic substance is preferably an organolithium compound because it can efficiently afford a compound that serves as the above-mentioned precursor. Specific examples of the organolithium compound include alkyl lithium compounds, such as methyl lithium, n-butyl lithium, sec-butyl lithium, and tert-butyl lithium; aryl lithium compounds, such as phenyl lithium; alkenyl lithium compounds, such as vinyl lithium; lithium amide compounds, such as lithium diisopropylamide and lithium bistrimethylsilylamide. Among these, the basic substance is preferably an alkyl lithium compound.

It is preferred that the basic substance be slowly added in an amount of from 2 to 4 equivalents, more preferably from 3 to 3.5 equivalents relative to the compound represented by general formula (9) that serves as a substrate, to the compound represented by general formula (9) under an inert gas atmosphere. When the basic substance is added, it is preferred to have diluted the compound represented by general formula (9) in a solvent. Although the kind of the solvent is not particularly restricted, an ether type solvent, particularly tetrahydrofuran, is preferred. Before the addition of the basic substance, the amount of the solvent relative to 1 mmol of the compound represented by general formula (9), which is not particularly limited, is preferred to be within the range of from 1 to 100 ml/mmol, more preferably within the range of from 1 to 50 ml/mmol, and even more preferably within the range of from 5 to 40 ml/mmol. When the compound represented by general formula (9) is reacted with the basic substance, a temperature is, not particularly limited to, preferably within the range of from −200 to 30° C. and more preferably within the range of from −80 to −10° C. When the compound represented by general formula (9) is reacted with the basic substance, a reaction time is preferably within the range of from 10 minutes to 4 hours and more preferably within the range of from 30 minutes to 2 hours.

The third production method of the present invention preferably includes the step of reacting the compound represented by general formula (9) with a basic substance, and further reacting the reaction product with at least one compound selected from the group consisting of magnesium compounds (e.g., MgCl$_2$, MgBr$_2$, and MgI$_2$), zinc compounds (e.g., ZnCl$_2$, ZnBr$_2$, and ZnI$_2$), tin compounds (e.g., organotin compounds, such as Sn$(R^2)_3$Cl, Sn$(R^2)_3$Br, and Sn$(R^2)_3$I (wherein $R^2$ is as defined above), boron compounds (e.g., boronic acid and boronic acid esters), and halogens (e.g., chlorine, bromine, and iodine) (the at least one compound may be hereinafter referred to as compound (M)). The reaction with compound (M) can be carried out by adding compound (M) to a reaction liquid after the reaction of the compound represented by general formula (9) with the basic substance. The amount of compound (M) is preferably within the range of from 1.0 to 2.0 equivalents, and more preferably within the range of from 1.02 to 1.1 equivalents relative to the compound represented by general formula (9) used as a substrate. The use of at least one compound selected from the group consisting of magnesium compounds, zinc compounds, tin compounds, and boron compounds as compound (M) makes it possible to produce directly the compound represented by general formula (10) or an anion compound having a structure resulting from the removal of an active proton from that compound.

In a case of using a halogen as compound (M), it is possible to obtain a compound resulting from the introduction of a halogen atom to $Q^2$ moiety in general formula (10) or an anion compound having a structure resulting from the removal of an active proton from that compound. Then, the halogen atom can be converted into $Q^2$, which is a reactive substituent, by reacting those compounds with Mg or Zn. Since the compound represented by general formula (10), the compound resulting from the introduction of a halogen atom to $Q^2$ moiety in general formula (10) or anion compounds having a structure resulting from the removal of an active proton from these compounds can be obtained more efficiently, it is preferred to bring the temperature of the reaction liquid into the range of from 0 to 80° C., more preferably the range of from 5 to 40° C. after the addition of compound (M). After bringing the temperature of the reaction liquid into the above-mentioned range, it is preferred to further stir the reaction liquid preferably for 10 minutes to 4 hours, more preferably for 30 minutes to 2 hours.

A compound represented by general formula (11) can be obtained by reacting (cross-coupling reaction) the compound represented by general formula (10) or the anion compound having a structure resulting from the removal of an active proton from that compound with a compound represented by general formula (8):

[Chem. 25]

$$Q^1\text{-W-}Q^1 \qquad (8)$$

wherein W is as defined above and each $Q^1$ is independently a halogen atom.

[Chem. 26]

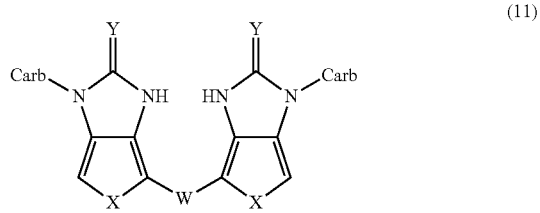

(11)

wherein X, Y, W, and Carb are as defined above.

Examples of the halogen atom that each $Q^1$ in the compound represented by general formula (8) represents include a fluorine atom, a chlorine atom, a bromine atom, and an iodine atom. The W in the compound represented by general formula (8) is preferably selected from the group consisting of an optionally substituted ethenylene group, optionally substituted arylene groups, and optionally substituted divalent heteroaromatic ring groups, more preferably an optionally substituted arylene group or an optionally substituted divalent heteroaromatic ring group.

As the reaction (cross-coupling reaction) of the compound represented by general formula (10) or the anion compound having a structure resulting from the removal of an active proton from that compound with the compound represented by general formula (8), for example, a Suzuki-Miyaura coupling reaction, a Migita-Kosugi-Stille coupling reaction, a Kumada-Corriu coupling reaction, a Negishi coupling reaction, and so on are suitably adopted. In a case of using the anion compound having a structure resulting from the removal of an active proton from the compound represented by general formula (10), the compound represented by general formula (11) can be obtained easily by, if necessary, adding an active proton-containing compound, such as water and alcohols, after the cross-coupling reaction.

It is preferred that the reaction of the compound represented by general formula (10) or the anion compound having a structure resulting from the removal of an active proton from that compound with the compound represented by general formula (8) be carried out in the presence of a solvent. Examples of such a solvent include saturated aliphatic or alicyclic hydrocarbons, such as pentane, hexane, heptane, octane, nonane, decane, and cyclohexane; aromatic hydrocarbons, such as benzene, toluene, ethylbenzene, propylbenzene, xylene, and ethyltoluene; ethers, such as dimethyl ether, ethyl methyl ether, diethyl ether, dipropyl ether, butyl methyl ether, tert-butyl methyl ether, dibutyl ether, tetrahydrofuran, and 1,4-dioxane; aprotic polar solvents, such as dimethylacetamide, dimethylformamide, N-methyl-2-pyrrolidone, and dimethyl sulfoxide. These solvents can be used alone or in combination of two or more. Among these, the solvent is preferably an ether and is more preferably diethyl ether, tetrahydrofuran, or 1,4-dioxane. The amount of the solvent is preferably within the range of 1 to 100 ml and more preferably within the range of 2 to 20 ml relative to 1 mmol of the compound represented by general formula (10) or an anion compound having a structure resulting from the removal of an active proton from that compound.

As a more specific example, in a case of reacting a compound represented by general formula (10) in which $Q^2$ is —Sn($R^2$)$_3$ with the compound represented by general formula (8), the above reaction can be carried out by dissolving these compounds in a solvent such as 1,4-dioxane, adding thereto a palladium catalyst, such as trans-dichlorobistriphenyl phosphine palladium, as a catalyst, and then refluxing the mixture.

In a similar manner to that in the above-described method in which the compound represented by general formula (10) and the compound represented by general formula (8) are subjected to a cross-coupling reaction, it is also possible to obtain the compound represented by general formula (11) by cross-coupling a compound resulting from the introduction of a halogen atom to $Q^2$ moiety in general formula (10) with a compound represented by general formula (6).

[Chem. 27]

$$Q^2\text{-W-}Q^2 \qquad (6)$$

wherein W and $Q^2$ are as defined above.

It is more preferred that the third production method of the present invention further include a step of eliminating at least one, preferably both, of the Carb's in the compound represented by general formula (11) obtained as described above. By the elimination of both the Carb's can be obtained a compound represented by general formula (12):

[Chem. 28]

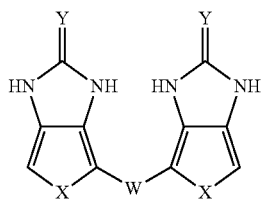
(12)

wherein X, Y, and W are as defined above.

In a case where the compound represented by general formula (12) is the desired compound represented by general formula (1) (that is, in a case where all the four Z's are hydrogen atoms in the compound represented by general formula (1)) in the third production method of the present invention, the desired compound can be obtained through the elimination of both the Carb's. The method of the elimination of Carb is not particularly restricted and techniques usually adopted for deprotection of a carbamate-type protective group can be used; for example, elimination can be done under a strongly acidic conditions, such as trifluoroacetic acid or an about 4 mol/l solution of hydrogen chloride in ethyl acetate when Carb is Boc, elimination can be done by a hydrogenation reaction using palladium as a catalyst or by Birch reduction when Carb is Cbz, elimination can be done using a secondary amine such as piperidine when Carb is Fmoc, elimination can be done by treating with zinc powder-acetic acid or the like when Carb is Troc, and elimination can be done by adding an amine or the like in the presence of a palladium catalyst when Carb is Alloc.

At least one, preferably all, of the plurality of Z's that the compound represented by general formula (1) to be produced in the third production method of the present invention can be an optionally substituted organic group having 1 to 20 carbon atoms. Such a compound represented by general formula (1) can be produced by, for example, removing at least one or all of the protons at N-positions in the compound represented by general formula (12) by a base such as sodium hydride, and then reacting the resultant product with a halide (e.g., an alkyl iodide).

In the present invention, the π-electron conjugated compound represented by general formula (1) is preferably synthesized from a compound represented by general formula (9) as in reactions a to d shown by chemical reaction formula (V) (fourth production method).

[Chem. 29]

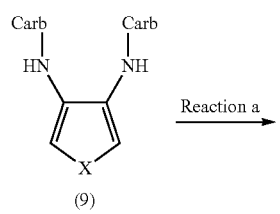
(9) Reaction a

-continued

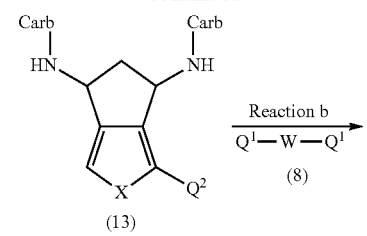
(13) Reaction b $Q^1—W—Q^1$ (8)

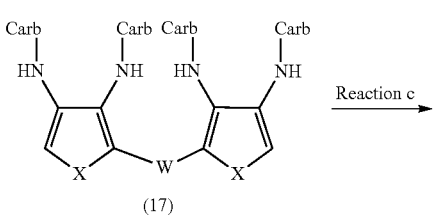
(17) Reaction c

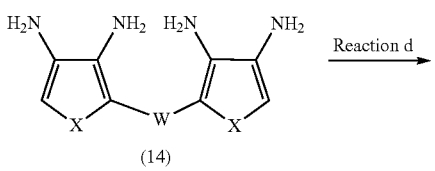
(14) Reaction d

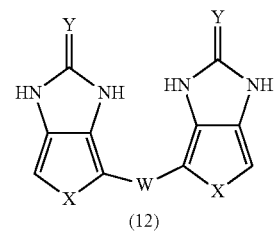
(12)

wherein X, Y, W, Carb, $Q^1$, and $Q^2$ are as defined above.

The fourth production method of the present invention includes the step of reacting the compound represented by general formula (9) with a basic substance to obtain a compound represented by general formula (13) or an anion compound having a structure resulting from the removal of an active proton from that compound.

[Chem. 30]

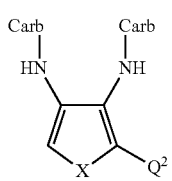
(13)

wherein X, Carb, and $Q^2$ are as defined above.

Specific examples of the anion compound having a structure resulting from the removal of an active proton from the compound represented by general formula (13) include an anion compound represented by general formula (13') or its tautomer or a compound in which an anion existing on a nitrogen atom in general formula (13') is delocalized together with a neighbouring π-electron.

[Chem. 31]

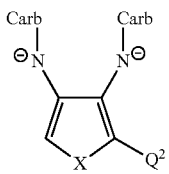
(13')

wherein X, Carb, and $Q^2$ are as defined above.

The counter cation of the anion compound depends on the kind of the basic substance to be used and so on, and examples thereof include cations of alkali metals, such as lithium ion, sodium ion, and potassium ion; cations of alkaline earth metals, such as magnesium ion and calcium ion; and ammonium ion. Such an anion compound is preferred when $Q^2$ is selected from the group consisting of —MgCl, —MgBr, —MgI, —ZnCl, —ZnBr, and —ZnI.

Although a compound capable of affording a compound that serves as a precursor of a compound represented by general formula (13) by reacting with a compound represented by general formula (9) can be used as the above-mentioned basic substance, the basic substance is preferably an organolithium compound because it can efficiently afford a compound that serves as the above-mentioned precursor. Specific examples of the organolithium compound include alkyl lithium compounds, such as methyl lithium, n-butyl lithium, sec-butyl lithium, and tert-butyl lithium; aryl lithium compounds, such as phenyl lithium; alkenyl lithium compounds, such as vinyl lithium; lithium amide compounds, such as lithium diisopropylamide and lithium bistrimethylsilylamide. Among these, the basic substance is preferably an alkyl lithium compound.

It is preferred that the basic substance be slowly added in an amount of from 2 to 4 equivalents, more preferably from 3 to 3.5 equivalents relative to the compound represented by general formula (9) that serves as a substrate, to the compound represented by general formula (9) under an inert gas atmosphere. When the basic substance is added, it is preferred to have diluted the compound represented by general formula (9) in a solvent. Although the kind of the solvent is not particularly restricted, an ether type solvent, particularly tetrahydrofuran, is preferred. Before the addition of the basic substance, the amount of the solvent relative to 1 mmol of the compound represented by general formula (9), which is not particularly limited, is preferred to be within the range of from 1 to 100 ml/mmol, more preferably within the range of from 1 to 50 ml/mmol, and even more preferably within the range of from 5 to 40 ml/mmol. When the compound represented by general formula (9) is reacted with the basic substance, a temperature is, not particularly limited to, preferably within the range of from –200 to 30° C. and more preferably within the range of from –80 to –10° C. When the compound represented by general formula (9) is reacted with the basic substance, a reaction time is preferably within the range of from 10 minutes to 4 hours and more preferably within the range of from 30 minutes to 2 hours.

The fourth production method of the present invention preferably includes the step of reacting the compound represented by general formula (9) with a basic substance, and then further reacting the reaction product with at least one compound selected from the group consisting of magnesium compounds (e.g., $MgCl_2$, $MgBr_2$, and $MgI_2$), zinc compounds (e.g., $ZnCl_2$, $ZnBr_2$, and $ZnI_2$), tin compounds (e.g., organotin compounds, such as $Sn(R^2)_3Cl$, $Sn(R^2)_3Br$, and $Sn(R^2)_3I$ (wherein $R^2$ is as defined above)), boron compounds (e.g., boronic acid and boronic acid esters), and halogens (e.g., chlorine, bromine, and iodine) (compound (M)). The reaction with compound (M) can be carried out by adding compound (M) to a reaction liquid after the reaction of the compound represented by general formula (9) with the basic substance. The amount of compound (M) is preferably within the range of from 1.0 to 2.0 equivalents, and more preferably within the range of from 1.02 to 1.1 equivalents relative to the compound represented by general formula (9) used as a substrate. The use of at least one compound selected from the group consisting of magnesium compounds, zinc compounds, tin compounds, and boron compounds as compound (M) makes it possible to produce directly the compound represented by general formula (13) or an anion compound having a structure resulting from the removal of an active proton from that compound.

In a case of using a halogen as compound (M), it is possible to obtain a compound resulting from the introduction of a halogen atom to $Q^2$ moiety in general formula (13) or an anion compound having a structure resulting from the removal of an active proton from that compound. Then, the halogen atom can be converted into $Q^2$, which is a reactive substituent, by reacting those compounds with Mg or Zn. Since the compound represented by general formula (13), the compound resulting from the introduction of a halogen atom to $Q^2$ moiety in general formula (13) or anion compounds having a structure resulting from the removal of an active proton from these compounds can be obtained more efficiently, the temperature of the reaction liquid is preferably controlled such that it may not become 10° C. or higher, more preferably so that it may not become 0° C. or higher, and even more preferably so that it may not become –10° C. or higher during a period after the addition of compound (M) until the stop of the reaction or the use in the following reaction.

A compound represented by general formula (14) can be obtained by reacting (cross-coupling reaction) the compound represented by general formula (13) or the anion compound having a structure resulting from the removal of an active proton from that compound with a compound represented by general formula (8):

[Chem. 32]

$$Q^1\text{-}W\text{-}Q^1 \qquad (8)$$

wherein W is as defined above and each $Q^1$ independently is a halogen atom.

[Chem. 33]

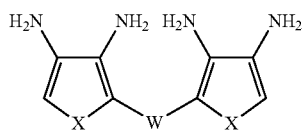
(14)

wherein X and W are as defined above.

Examples of the halogen atom that each $Q^1$ in the compound represented by general formula (8) represents include a fluorine atom, a chlorine atom, a bromine atom, and an iodine atom. The W in the compound represented by general formula (8) is preferably selected from the group consisting of an optionally substituted ethenylene group, optionally substituted arylene groups, and optionally substituted divalent heteroaromatic ring groups, more preferably an optionally substituted arylene group or an optionally substituted divalent heteroaromatic ring group.

As the reaction (cross-coupling reaction) of the compound represented by general formula (13) or the anion compound having a structure resulting from the removal of an active proton from that compound with the compound represented by general formula (8), for example, a Suzuki-Miyaura coupling reaction, a Migita-Kosugi-Stille coupling reaction, a Kumada-Corriu coupling reaction, a Negishi coupling reaction, and so on are suitably adopted.

It is preferred that the reaction of the compound represented by general formula (13) or the anion compound having a structure resulting from the removal of an active proton from that compound with the compound represented by general formula (8) be carried out in the presence of a solvent. Examples of such a solvent include saturated aliphatic or alicyclic hydrocarbons, such as pentane, hexane, heptane, octane, nonane, decane, and cyclohexane; aromatic hydrocarbons, such as benzene, toluene, ethylbenzene, propylbenzene, xylene, and ethyltoluene; ethers, such as dimethyl ether, ethyl methyl ether, diethyl ether, dipropyl ether, butyl methyl ether, tert-butyl methyl ether, dibutyl ether, tetrahydrofuran, and 1,4-dioxane; aprotic polar solvents, such as dimethylacetamide, dimethylformamide, N-methyl-2-pyrrolidone, and dimethyl sulfoxide. The solvents can be used alone or in combination of two or more. Among these, the solvent is preferably an ether and is more preferably diethyl ether, tetrahydrofuran, or 1,4-dioxane. The amount of the solvent is preferably within the range of 1 to 100 ml and more preferably within the range of 2 to 20 ml relative to 1 mmol of the compound represented by general formula (13) or an anion compound having a structure resulting from the removal of an active proton from that compound.

As a more specific example, in a case of reacting a compound represented by general formula (13) in which $Q^2$ is —$Sn(R^2)_3$ with the compound represented by general formula (8), the above reaction can be carried out by dissolving these compounds in a solvent such as 1,4-dioxane, adding thereto a palladium catalyst, such as trans-dichlorobistriphenyl phosphine palladium, as a catalyst, and then refluxing the mixture.

In a similar manner to that in the above-described method in which the compound represented by general formula (13) and the compound represented by general formula (8) are subjected to a cross-coupling reaction, it is also possible to obtain the compound represented by general formula (14) by cross-coupling a compound resulting from the introduction of a halogen atom to $Q^2$ moiety in general formula (13) with a compound represented by general formula (6).

[Chem. 34]

wherein W and $Q^2$ are as defined above.

The compound represented by general formula (14) can be obtained by reacting (cross-coupling reaction) the compound represented by general formula (13) or the anion compound having a structure resulting from the removal of an active proton from that compound with the compound represented by general formula (8) and then eliminating the Carb in the resulting compound. The method of the elimination of Carb is not particularly restricted and techniques usually adopted for deprotection of a carbamate-type protective group can be used; for example, elimination can be done under a strongly acidic conditions, such as trifluoroacetic acid or an about 4 mol/l solution of hydrogen chloride in ethyl acetate when Carb is Boc, elimination can be done by a hydrogenation reaction using palladium as a catalyst or by Birch reduction when Carb is Cbz, elimination can be done using a secondary amine such as piperidine when Carb is Fmoc, elimination can be done by treating with zinc powder-acetic acid or the like when Carb is Troc, and elimination can be done by adding an amine or the like in the presence of a palladium catalyst when Carb is Alloc.

In a case of using the anion compound having a structure resulting from the removal of an active proton from the compound represented by general formula (13), a proton can be introduced into an anionic moiety, if necessary, by adding an active proton-containing compound, such as water and alcohols, after the cross-coupling reaction.

The compound represented by general formula (12) can be obtained by reacting the compound represented by general formula (14) react with a urea bond- or thiourea bond-forming compound. While urea, phosgene, chloroformic acid esters, carbonyldiimidazole, and so on can be used as the urea bond-forming compound and thiourea, isothiocyanate compounds, and so on can be used as the thiourea bond-forming compound, it is preferred, from the viewpoint of industrial production, such as load on the environment, to use urea or phosgene, and it is more preferred to use urea. This reaction is carried out preferably in the presence of a solvent. Examples of the solvent include saturated aliphatic or alicyclic hydrocarbons, such as pentane, hexane, heptane, octane, nonane, decane, and cyclohexane; aromatic hydrocarbons, such as benzene, toluene, ethylbenzene, propylbenzene, xylene, and ethyltoluene; ethers, such as dimethyl ether, ethyl methyl ether, diethyl ether, dipropyl ether, butyl methyl ether, tert-butyl methyl ether, dibutyl ether, tetrahydrofuran, and 1,4-dioxane; aprotic polar solvents, such as a dimethylacetamide, dimethylformamide, N-methyl-2-pyrrolidone, and dimethyl sulfoxide; alcohols, such as butanol and amyl alcohol. When urea is used as a urea bond-forming compound, it is preferred to select, among these solvents, an appropriate solvent such that the reaction temperature does not exceed 140° C. The amount of such a solvent is preferably within the range of from 1 to 100 ml, and more preferably within the range of from 2 to 10 ml relative to 1 mmol of the compound represented by general formula (14).

At least one, preferably all, of the plurality of Z's that the compound represented by general formula (1) to be produced in the fourth production method of the present invention can be an optionally substituted organic group having 1 to 20 carbon atoms. Such a compound represented by general formula (1) can be produced by, for example, removing at least one or all of the protons at N-positions in the compound represented by general formula (12) with a base such as sodium hydride, and then reacting the resultant with a halide (e.g., an alkyl iodide).

The compound represented by general formula (1) to be obtained by the production method of the present invention can be used as a monomer component for producing a π-electron conjugated polymer. Particularly because the π-electron conjugated polymer has a constitutional unit in which two heterocyclic structures are linked via W, it is possible to form a π-electron conjugated polymer capable of exhibiting a desired colored state by properly changing the kind of the W by selecting the compound represented by general formula (1) used. Therefore, it becomes possible to provide a π-electron conjugated polymer which changes the color thereof from a desired colored state to a colorless decolored state, and the π-electron conjugated polymer can be suitably used as a base material that constitutes a coloring layer of an electrochromic display device.

In the present invention, a π-electron conjugated polymer represented by general formula (2) is obtained from the π-electron conjugated compound represented by general formula (1) obtained in the manner described above as mentioned above, like reaction 6 represented by reaction formula (VI):

[Chem. 35]

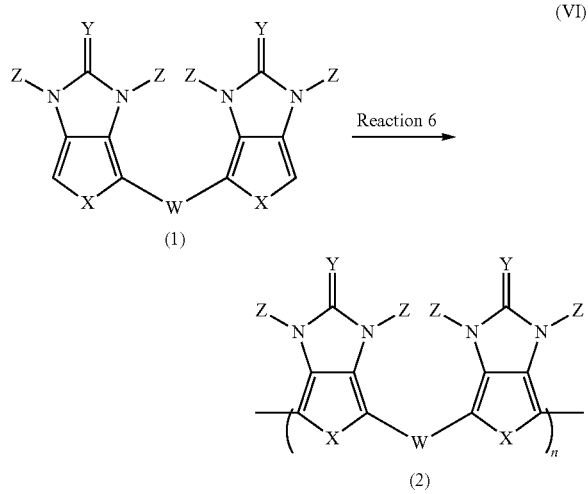

wherein X, Y, Z, and W are as defined above, and n is an integer of 2 or greater.

Reaction 6 shown above is a reaction of obtaining a π-electron conjugated polymer represented by general formula (2) by a polymerization reaction from a π-electron conjugated compound that is a monomer compound represented by general formula (1). The polymerization reaction of reaction 6 shown above is not particularly restricted and examples thereof include a method of performing electrochemical polymerization (hereinafter, sometimes abbreviated as electrolytic polymerization), and a method of performing polymerization by chemical oxidation (hereinafter, sometimes abbreviated as chemical oxidation polymerization), to obtain a polymer by removing hydrogen from a monomer component using an oxidizing agent which is a transition metal salt, typically ferric chloride ($FeCl_3$), iron perchlorate, copper perchlorate, and so on. A method that comprises preparing a solution in which a monomer component to serve as a raw material to be polymerized is dissolved in a solvent or an electrolytic solution by further dissolving a supporting electrolyte in that solution, and applying a voltage between electrodes through the solution or electrolytic solution, to obtain a desired polymer on an anode is adopted favorably as a specific method of polymerizing by electrolytic polymerization. The polymer is provided as a film. Thus, a film suitable as a material for constituting an electrochromic display device can be formed by electrolytic polymerization, and it becomes possible to produce an electrochromic display device in a high productivity. Moreover, the adoption of electrolytic polymerization also has an advantage that the production of an EC display device becomes easy because the adoption makes it possible to directly produce a member in which a layer containing a π-electron conjugated polymer and an electrode have been integrated and such a member can be used as it is as a constituent member of an EC display device as described later.

Examples of the solvent that can be used in the above-mentioned electrolytic polymerization include nitromethane, acetonitrile, propylene carbonate, nitrobenzene, cyanobenzene, o-dichlorobenzene, dimethyl sulfoxide, gamma-butyrolactone, dimethyl ether, and water. Examples of a supporting electrolyte to be used for an electrolytic solution include a supporting salt composed of a cation, such as alkali metal ions, such as lithium ion, potassium ion, and sodium ion, and quaternary ammonium ion and anions, such as perchlorate ion, boron tetrafluoride ion, phosphorus hexafluoride ion, halogen atom ions, arsenic hexafluoride ion, antimony hexafluoride ion, sulfate ion, and hydrogen sulfate ion. It is permissible also to use as an electrolytic solution, for example, a solution prepared by dissolving the above-mentioned compound represented by general formula (1) (monomer component) in an ionic liquid prepared by combining a cation and an anion, where the cation is an ammonium-type ion, such as imidazolium salts and pyridinium salts; a phosphonium type ion; an inorganic ion; a halogen ion; or the like and the anion is a fluorine-containing ion, such as fluoride ion and triflate.

The content of the above-mentioned compound represented by general formula (1) (monomer component), which can be appropriately determined depending on the polymerization reaction conditions and so on, is preferably within the range of from 0.001 to 10 mol/l and more preferably is within the range of from 0.01 to 0.1 mol/l. The content of the supporting electrolyte in the above-mentioned electrolytic solution is preferably within the range of from 0.01 to 10 mol/l and more preferably is within the range of from 0.1 to 5 mol/l.

The above-mentioned electrode material is not particularly restricted and, for example, metals, such as platinum, gold, nickel, and silver; conductive polymers; ceramics; semiconductors; conductive carbides, such as carbon and conductive diamond; metal oxides, such as ITO (indium tin oxide), ATO (antimony-doped tin dioxide), AZO (aluminum-doped zinc oxide), and ZnO (zinc oxide); and so on can be used.

The voltage at the time of applying a voltage, which can be appropriately determined depending on the polymerization reaction conditions and so on, is preferably within the range of from −3 to 3 V and more preferably is within the range of from −1.5 to 1.5 V relative to a silver-silver chloride reference electrode. The temperature at the time of applying a voltage is preferably within the range of from 0 to 80° C. and more preferably is within the range of from 15 to 40° C.

The π-electron conjugated polymer produced using the compound represented by general formula (1) obtained by the production method of the present invention as a monomer component as described above can be suitably used as a material that constitutes the coloring layer of an EC display device. An EC display device has at least a pair of electrodes, and usually a layer containing the aforementioned π-electron conjugated polymer is disposed between the electrodes. The shape of the electrodes is not particularly restricted and may be appropriately designed depending upon a desired EC display device and, for example, plate-shaped electrodes can be used. The material that constitutes the electrodes is not particularly restricted and metals, conductive macromolecules, ceramics, semiconductors, conductive carbides, and so on can be used. In an EC display device with which an observer views a coloring layer through one of the electrodes, the electrode is preferably transparent. Examples of the material to constitute such a transparent electrode include metal oxides, such as ITO, ATO, AZO, and ZnO; conductive carbides, such as SWCNT (single wall carbon nanotube) and DWCNT (double wall carbon nanotube); conductive polymers, such as PEDOT (poly(ethylene-3,4-dioxythiophene)), polyaniline derivatives, and polypyrrole derivatives.

Although the layer containing the π-electron conjugated polymer may be constituted by the π-electron conjugated polymer alone, it may contain other components as long as the performance as an EC display device, or the like is not impaired. Examples of such other components include compounds that exhibit chromic properties through an oxidation-reduction reaction, such as π-electron conjugated carbides, e.g., SWCNT, DWCNT, and fullerene; viologen or its derivatives, prussian blue or its derivatives, and tungstic oxide or its derivatives. The content of the π-electron conjugated polymer in the layer containing the π-electron conjugated polymer is preferably 50% by weight or more and more preferably 80% by weight or more.

An EC display device preferably has an insulating substrate on the outer surface of at least one of the two electrodes, more preferably on the outer surfaces of both the electrodes for the purpose of, for example, protecting an electrode. Examples of the material that constitutes the insulating substrate include glass, such as quartz glass and white sheet glass; ceramics; paper; wood; and synthetic resins. Examples of the synthetic resins include polyester resins, such as polyethylene naphthalate, and polyethylene terephthalate; polyamides; polycarbonates; cellulose esters, such as cellulose acetate; fluorine-containing polymers, such as polyvinylidene fluoride and poly(tetrafluoroethylene-co-hexafluoropropylene); polyethers, such as polyoxymethylene; polyacetal; polystyrene; polyolefins, such as polyethylene, polypropylene, and polymethylpentene; polyimides, such as polyamide-imide and polyetherimide. In an EC display device with which an observer views a coloring layer through one electrode as described above, the insulating substrate that is to disposed on the outer surface of one transparent electrode is preferably also a transparent substrate (an insulating substrate preferably having a total light transmittance of 70% or more, more preferably 80% or more). Examples of the material that constitutes such a transparent insulating substrate include glass, such as quartz glass and white glass; and macromolecules, such as polystyrene, polymethyl methacrylate, styrene-methyl methacrylate copolymers, polycarbonates, cycloolefin polymers, cycloolefin copolymers, polyethylene terephthalate, and polyethylene naphthalate.

When a voltage is applied to the layer containing the π-electron conjugated polymer (the coloring layer), the π-electron conjugated polymer releases or receives electrons to change into a polymer having a structure that is called a quinoid structure. As a result, the conjugation length of electrons in the π-electron conjugated polymer changes, so that a light absorption wavelength changes and an electrochromic properties are developed. An operation of changing a polymer to a polymer having this quinoid structure is called doping. Since the quinoid structure is a charged unit, an ionic species formed by ionization of an electrolyte for maintaining the charge neutrality usually exists near a π-electron conjugated polymer having the quinoid structure. This ionic species is called a dopant. Although it is known that the absorption wavelength of a π-electron conjugated polymer usually shifts toward the long-wavelength side by doping, the use of the π-electron conjugated polymer makes it possible to form a film (a coloring layer) for EC display devices that changes, due to doping, from a colored state at the time of dedoping to a decolored state in which a large absorption is not exhibited in the visible light range.

The dopant to be used is not particularly restricted, and examples thereof include halogenated anions of Group 5B elements, such as $PF_6^-$, $SbF_6^-$, and $AsF_6^-$; halogenated anions of Group 3B elements, such as $BF_4^-$; halogen anions, such as I− ($I_3^-$), Br−, and Cl−; halogen acid anions, such as $ClO_4^-$; metal halide anions, such as $AlCl_4^-$, $FeCl_4^-$, and $SnCl_5^-$; a nitrate anion represented by $NO_3^-$; a sulfate anion represented by $SO_4^{2-}$; organic sulfonic acid anions, such as a p-toluenesulfonic acid anion, a naphthalene sulfonic acid anion, $CH_3SO_3^-$, and $CF_3SO_3^-$; carboxylic acid anions, such as $CF_3COO^-$ and $C_6H_5COO^-$; and modified polymers having the above-mentioned anion species in their main chains or side chains. Dopants can be used alone or in combination of two or more. The mode of the addition of the dopant is not particularly restricted, and examples thereof include a method that comprises providing an electrolyte layer containing the dopant adjacent to a layer containing the π-electron conjugated polymer in an EC display device, and forcing the dopant to move to the vicinity of the π-electron conjugated polymer by the application of a voltage in operating the EC display device, and a method that comprises making a layer containing the π-electron conjugated polymer contain the dopant in advance. The electrolyte layer may be any of a solid, a gel, and a liquid. When the π-electron conjugated polymer formed by electrolytic polymerization on an electrode that is an anode is used together with the electrode as a constituent member of an EC display device without being removed from the electrode, an anion derived from the supporting electrolyte used in the electrolytic polymerization can be used, as it is, as a dopant. When polymerization is carried out by chemical oxidation polymerization, an anion derived from an oxidizing agent to be used can be used, as it is, as a dopant.

In an EC display device, it is preferred to provide a spacer in at least a part of the space between the pair of electrodes because the distance between the electrodes can be held and short circuit can be prevented. Examples of the material constituting the spacer include resins, such as epoxy resins, acrylic resins, polyester resins, polyether resins, polyethylene resins, and polyimide resins; inorganic oxides; and their hybrid materials.

Although there are no particular limitations to the method for producing an EC display device and, for example, an EC display device can be produced by separately preparing constituent members, such as a layer containing the π-electron conjugated polymer, an electrode, an insulating substrate, an electrolyte layer, and a spacer, and then assembling them, preferred is a method in which a layer containing the above-mentioned π-electron conjugated polymer is formed on an electrode in advance and an EC display device is produced using a member which has the layer and the electrode integrated with each other, and it is more preferred to polymerize, by electrolytic polymerization, the compound (monomer component) represented by general formula (1) on an anodic electrode and produce an EC display device by using the resulting π-electron conjugated polymer together with an electrode as constituent members of the EC display device without removing the polymer from the electrode because an EC display device can be more conveniently produced.

The π-electron conjugated polymer produced using the compound represented by general formula (1) to be obtained by the production method of the present invention as a monomer component can be used for applications other than the application as a material to constituting EC display devices, and it can be used, for example, for various applications as shaped articles of a film, a fiber, a solid capacitor, an organic photoelectric conversion device, an anticorrosion paint, a memory device, an organic field effect transistor, and so on. In the case where the above-mentioned π-electron conjugated polymer is doped to form a polymer having a quinoid structure in which dopants exist near to each other, the polymer becomes an electrically conductive polymer having a low band gap and, therefore, it can be suitably used as an highly-conductive ionic polymer especially for applications where electrical conductivity is required.

EXAMPLES

The present invention will be described more specifically by way of Examples.

Production Example 1

Synthesis of 1H-thieno[3,4-d]imidazol-2(3H)-one represented by formula (3a)

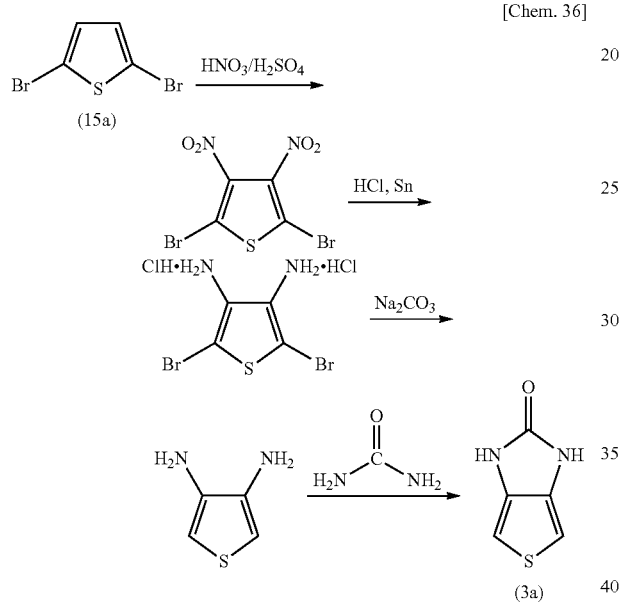

A mixed acid was prepared using 11 ml of fuming nitric acid and 20 ml of fuming sulfuric acid. To a solution prepared by adding 13 ml of concentrated sulfuric acid to that mixed acid was dropped slowly 7.5 g (31 mmol) of 2,5-dibromothiophene represented by formula (15a), and stirring was done for 3 hours while the temperature was kept at 20 to 30° C. with a water bath, and then the reaction was stopped by transferring the liquid in a flask to a container containing 90 g of ice. The resulting solid was collected by filtration and it was recrystallized using methanol, so that 2,5-dibromo-3,4-dinitrothiophene was obtained. The yield based on 2,5-dibromothiophene was 66%. To the resulting 2,5-dibromo-3,4-dinitrothiophene was added 12 N concentrated hydrochloric acid at a rate of 6.05 ml/mmol. While the temperature of the resulting solution was kept at 0° C. with an ice bath, tin in an amount of 7.1 equivalents to 2,5-dibromo-3,4-dinitrothiophene was added slowly, followed by stirring for additional 2 hours. Then, the formed solid was collected by filtration and the solid was washed with diethyl ether, so that 3,4-diaminothiophene dihydrochloride was obtained. The yield based on 2,5-dibromo-3,4-dinitrothiophene was 90%.

The result of the $^1$H-NMR measurement of 3,4-diaminothiophene dihydrochloride is shown below.

$^1$H-NMR (500 MHz, DMSO, TMS) δ: 6.95 (2H, s)

The resulting 3,4-diaminothiophene dihydrochloride was dissolved in water in an amount equivalent to 4 ml/mmol, and a 4N aqueous sodium carbonate solution in an amount equivalent to 2 ml/mmol was dropped thereto slowly, followed by stirring for additional 2 hours after the dropping. The product was extracted to an organic layer using ethyl acetate and the resulting organic layer was dried over sodium sulfate and then the solvent was distilled off, so that 3,4-diaminothiophene was obtained. The yield based on 3,4-diaminothiophene dihydrochloride was 60%.

The result of the $^1$H-NMR measurement of 3,4-diaminothiophene is shown below.

$^1$H-NMR (500 MHz, CDCl$_3$, TMS) δ: 6.17 (2H, s), 3.36 (4H, s)

To the resulting 3,4-diaminothiophene were added 1.1 equivalents of urea and 10 ml/mol of amyl alcohol and a reaction was advanced under reflux at 130° C. for 5 hours in an argon gas atmosphere, and then the amyl alcohol was evaporated, followed by a purification step by column separation using an ethyl acetate/hexane solvent, so that 1H-thieno[3,4-d]imidazol-2(3H)-one represented by formula (3a) was obtained. The yield was 60%.

The result of the $^1$H-NMR measurement of 1H-thieno[3,4-d]imidazol-2(3H)-one is shown below.

$^1$H-NMR (500 MHz, CDCl$_3$, TMS) δ: 6.36 (1H, s)

Example 1

Synthesis of 4-[4-(2-oxo-2,3-dihydro-1H-thieno[3,4-d]imidazol-4-yl)phenyl]-1H-thieno[3,4-d]imidazol-2(3H)-one represented by formula (1a) and a polymer represented by formula (2a)

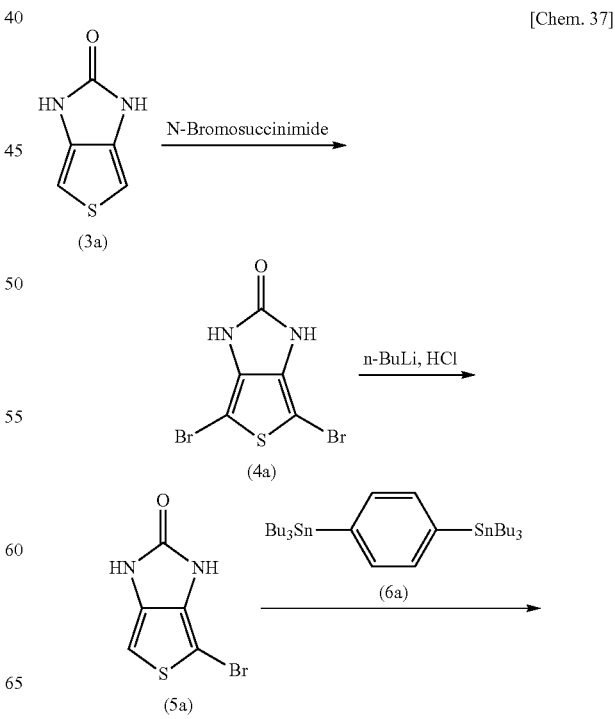

-continued

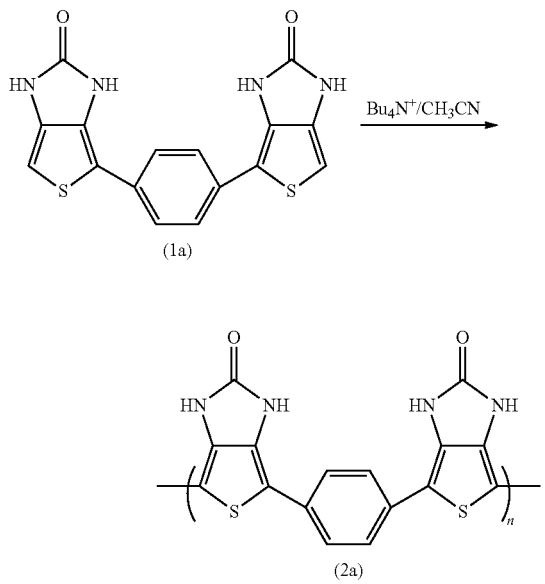

The resulting 1H-thieno[3,4-d]imidazol-2(3H)-one represented by formula (3a) was dissolved in 10 ml/mmol of tetrahydrofuran and was kept at −78° C. in a dry ice-cooled methanol bath. To this was dropped slowly 2.1 equivalents of N-bromosuccinic imide dissolved in tetrahydrofuran of an amount of 5 ml/mmol relative to the 1H-thieno[3,4-d]imidazol-2(3H)-one represented by formula (3a), followed by a reaction for 30 minutes, and then the reaction was stopped by adding an excessive amount of a saturated aqueous sodium chloride solution. The product was extracted from the reaction liquid to an organic layer using diethyl ether and dried over sodium sulfate and then the solvent was evaporated, followed by a purification step by column separation using an ethyl acetate/hexane solvent, so that 4,6-dibromo-1H-thieno[3,4-d]imidazol-2(3H)-one represented by formula (4a) was obtained. The yield was 90%.

The result of the $^1$H-NMR measurement of 4,6-dibromo-1H-thieno[3,4-d]imidazol-2(3H)-one is shown below.

$^1$H-NMR (500 MHz, DMSO, TMS) δ: 11.01 (2H, s)

The resulting 4,6-dibromo-1H-thieno[3,4-d]imidazol-2(3H)-one represented by formula (4a) was dissolved in 10 ml/mmol of dry tetrahydrofuran and was kept at −78° C. in a dry ice-cooled methanol bath. Under argon gas atmosphere, a 1.6 N n-butyl lithium/hexane solution in an amount of 3.1 equivalents relative to 4,6-dibromo-1H-thieno[3,4-d]imidazol-2(3H)-one represented by formula (4a) was dropped slowly, followed by a reaction for 15 minutes, and then the reaction was stopped by the addition of 5 equivalents of 1N hydrochloric acid. The product was extracted from the reaction liquid to an organic layer using diethyl ether and dried over sodium sulfate and then the solvent was evaporated, followed by a purification step by column separation using an ethyl acetate/hexane solvent, so that 4-bromo-1H-thieno[3,4-d]imidazol-2(3H)one represented by formula (5a) was obtained. The yield was 60%.

The result of the $^1$H-NMR measurement of 4-bromo-1H-thieno[3,4-d]imidazol-2(3H)one is shown below.

$^1$H-NMR (500 MHz, DMSO, TMS) δ: 6.51 (1H, s), 10.50 (1H, s), 10.77 (1H, s)

1,4-Dibromobenzene was dissolved in 2 ml/mmol of dry tetrahydrofuran and was kept at −78° C. in a dry ice-cooled methanol bath. Under argon gas atmosphere, a 1.6 N n-butyl lithium/hexane solution in an amount of 1.1 equivalents relative to 1,4-dibromobenzene was dropped slowly, followed by a reaction for 30 minutes, and then 1.0 equivalent of tributyltin chloride was added, followed by a reaction for 1 hour. Moreover, a 1.6 N n-butyl lithium/hexane solution in an amount of 1.1 equivalents relative to 1,4-dibromobenzene was dropped slowly, followed by a reaction for 30 minutes, and then 1.0 equivalent of tributyltin chloride was added, followed by a reaction for 1 hour, and then the reaction was stopped by the addition of an excessive amount of a saturated aqueous sodium chloride solution. Washing was done three times using a saturated aqueous sodium chloride solution, then the product was separately extracted from the resulting reaction liquid to an organic layer using diethyl ether, followed by drying over sodium sulfate, and then the solvent was evaporated, so that 1,4-ditributyltinbenzene was obtained.

The result of the $^1$H-NMR measurement of 1,4-ditributyltinbenzene is shown below.

$^1$H-NMR (500 MHz, CDCl$_3$, TMS) δ: 7.40 (4H, s), 1.54 (12H, quint.), 1.32 (12H, h), 1.03 (12H, t), 0.88 (18H, t)

To 1,4-ditributyltinbenzene were added 2.0 equivalents of 4-bromo-1H-thieno[3,4-d]imidazol-2(3H)-one represented by formula (5a), 5 ml/mol of dry toluene, and 0.2 equivalents of trans-dichlorobistriphenylphosphine palladium, then a reaction was advanced under reflux at 130° C. for 40 hours in an argon gas atmosphere, and then the reaction was stopped by the addition of a saturated aqueous ammonium chloride solution. The product was extracted from the resulting reaction liquid to an organic layer using diethyl ether, followed by drying over sodium sulfate, and then the solvent was evaporated, followed by a purification step by column separation using an ethyl acetate/hexane solvent, so that 4-[4-(2-oxo-2,3-dihydro-1H-thieno[3,4-d]imidazol-4-yl)phenyl]-1H-thieno[3,4-d]imidazol-2(3H)-one represented by formula (1a) was obtained.

The result of the $^1$H-NMR measurement of 4-[4-(2-oxo-2,3-dihydro-1H-thieno[3,4-d]imidazol-4-yl)phenyl]-1H-thieno[3,4-d]imidazol-2(3H)-one is shown below.

$^1$H-NMR (500 MHz, CDCl$_3$, TMS) δ: 6.33 (2H, s), 7.44 (4H, s)

The resulting compound represented by formula (1a) was dissolved in a concentration of 0.01M or less in a 0.1 M tetrabutylammonium/acetonitrile solution and then was electrochemically polymerized by the application of a potential at a sweeping rate of 100 mV/sec over the range of from 0 to 1.27 V, so that a film of a polymer represented by formula (2a) was formed. When the electrochromic properties of the resulting film were examined by using a UV-Vis spectrum (ultraviolet-visible absorption spectrum), it was confirmed that an M color with an absorbance maximum around 500 nm was developed at the time of coloration (dedoping) and there was no absorbance maximum in the visible range at the time of decoloration (doping).

Example 2

Synthesis of 4-[9-methyl-6-(2-oxo-2,3-dihydro-1H-thieno[3,4-d]imidazol-4-yl)-9H-carbazol-3-yl]-1H-thieno[3,4-d]imidazol-2(3H)-one represented by formula (1b) and a polymer represented by formula (2b)

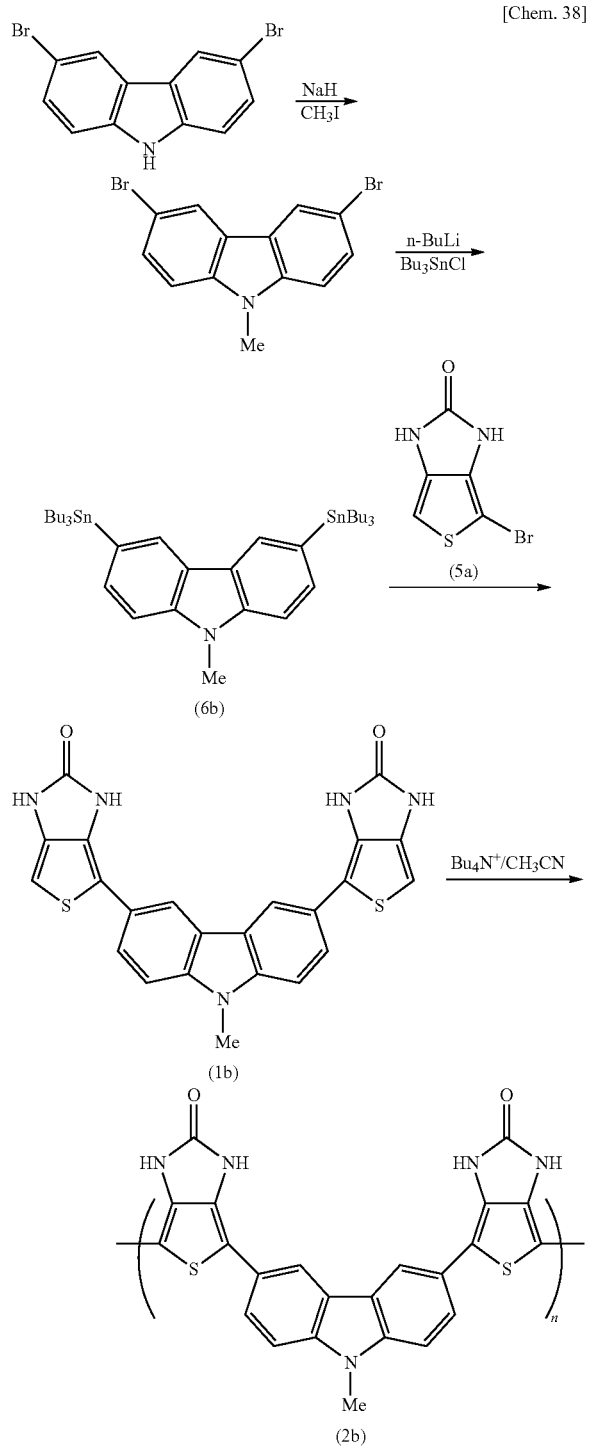

4-Bromo-1H-thieno[3,4-d]imidazol-2(3H)-one represented by formula (5a) was obtained in the same manner as in Example 1. In 3 ml/mmol of tetrahydrofuran to 3,6-dibromo-9H-carbazole, it was reacted with 1.1 equivalents of sodium hydride for 1 hour under argon gas atmosphere while being kept at 0° C. in an ice bath, and then 1.2 equivalents of methyl iodide was added and a reaction was further continued for 4 hours at room temperature. The reaction was stopped by adding an excessive amount of a mixed aqueous solution of ion-exchange water:ammonium chloride=3:1. The product was extracted from the resulting reaction liquid to an organic layer using diethyl ether and dried over sodium sulfate and then the solvent was evaporated, followed by a purification step by column separation using an ethyl acetate/hexane solvent, so that 3,6-dibromo-9-methyl-9H-carbazole was obtained.

The result of the $^1$H-NMR measurement of 3,6-dibromo-9-methyl-9H-carbazole is shown below.

$^1$H-NMR (500 MHz, DMSO, TMS) δ: 3.87 (3H, s), 7.61 (2H, d), 7.62 (2H, d), 8.47 (2H, s)

3,6-Dibromo-9-methyl-9H-carbazole was dissolved in 2 ml/mmol of dry tetrahydrofuran and was kept at −78° C. in a dry ice-cooled methanol bath. Under argon gas atmosphere, a 1.6 N n-butyl lithium/hexane solution in an amount of 1.1 equivalents relative to 3,6-dibromo-9-methyl-9H-carbazole was dropped slowly, followed by a reaction for 30 minutes, and then 1.0 equivalent of tributyltin chloride was added, followed by a reaction for 1 hour. Moreover, a 1.6 N n-butyl lithium/hexane solution in an amount of 1.1 equivalents relative to 3,6-dibromo-9-methyl-9H-carbazole was dropped slowly, followed by a reaction for 30 minutes, and then 1.0 equivalent of tributyltin chloride was added, followed by a reaction for 1 hour, and then the reaction was stopped by the addition of an excessive amount of a saturated aqueous sodium chloride solution. The reaction liquid was washed three times with a saturated aqueous sodium chloride solution, then the product was extracted from the resulting reaction liquid to an organic layer using diethyl ether, followed by drying over sodium sulfate, and then the solvent was evaporated, so that 3,6-ditributyltin-9-methyl-9H-carbazole represented by formula (6b) was obtained.

The result of the $^1$H-NMR measurement of 3,6-ditributyltin-9-methyl-9H-carbazole is shown below.

$^1$H-NMR (500 MHz, CDCl$_3$, TMS) δ: 1.59 (12H, quint.), 1.38 (12H, h), 1.13 (12H, t), 0.91 (18H, t), 3.82 (3H, s), 7.38 (2H, d), 7.51 (2H, d), 8.18 (2H, s)

To 3,6-ditributyltin-9-methyl-9H-carbazole represented by formula (6b) were added 2.0 equivalents of 4-bromo-1H-thieno[3,4-d]imidazol-2(3H)-one represented by formula (5a), 5 ml/mol of dry toluene, and 0.2 equivalents of trans-dichlorobistriphenylphosphine palladium, then a reaction was advanced under reflux at 130° C. for 40 hours in an argon gas atmosphere, and then the reaction was stopped by the addition of an excessive saturated aqueous ammonium chloride solution. The product was extracted from the resulting reaction liquid to an organic layer using diethyl ether, followed by drying over sodium sulfate, and then the solvent was evaporated, followed by a purification step by column separation using an ethyl acetate/hexane solvent, so that 4-[9-methyl-6-(2-oxo-2,3-dihydro-1H-thieno[3,4-d]imidazol-4-yl)-9H-carbazol-3-yl]-1H-thieno[3,4-d]imidazol-2(3H)-one represented by formula (1b) was obtained.

The result of the $^1$H-NMR measurement of 4-[9-methyl-6-(2-oxo-2,3-dihydro-1H-thieno[3,4-d]imidazol-4-yl)-9H-carbazol-3-yl]-1H-thieno[3,4-d]imidazol-2(3H)-one is shown below.

$^1$H-NMR (500 MHz, CDCl$_3$, TMS) δ: 3.88 (3H, s), 6.30 (2H, s), 7.43 (2H, d), 7.58 (2H, d), 8.18 (2H, s)

The resulting compound represented by formula (1b) was dissolved in a concentration of 0.01M or less in a 0.1 M tetrabutylammonium/acetonitrile solution and then was electrochemically polymerized by the application of a potential at a sweeping rate of 100 mV/sec over the range of from 0 to 1.00 V, so that a film of a polymer represented by formula (2b) was formed. When the electrochromic properties of the resulting film were examined by using a UV-Vis spectrum, it was confirmed that a Y color with an absorbance maximum around 400 nm was developed at the time of coloration (de-doping) and there was no absorbance maximum in the visible range at the time of decoloration (doping).

Example 3

Synthesis of 4-[7-(2-oxo-2,3-dihydro-1H-thieno[3,4-d]imidazol-4-yl)-2,3-dihydrothieno[3,4-b][1,4]dioxin-5-yl]-1H-thieno[3,4-d]imidazol-2(3H)-one represented by formula (1c) and a polymer represented by formula (2c)

[Chem. 39]

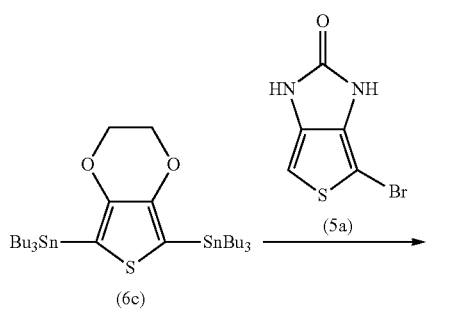

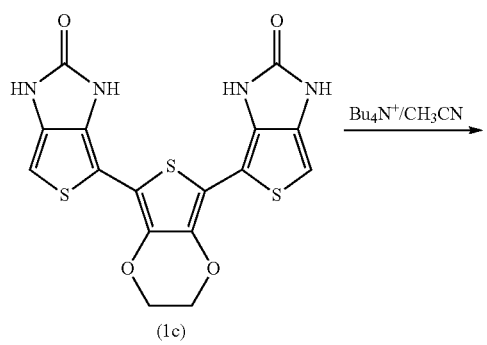

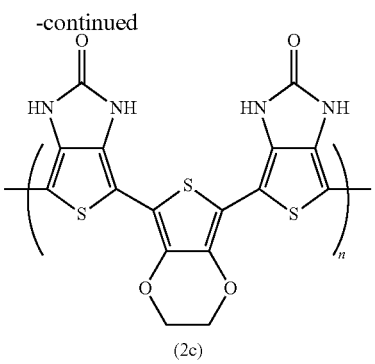

4-Bromo-1H-thieno[3,4-d]imidazol-2(3H)-one represented by formula (5a) was obtained in the same manner as in Example 1. 2,3-Dihydrothieno[3,4-b][1,4]dioxin was dissolved in 2 ml/mmol of dry tetrahydrofuran and was kept at −78° C. in a dry ice-cooled methanol bath. Under argon gas atmosphere, a 1.6N n-butyl lithium/hexane solution in an amount of 1.1 equivalents relative to 2,3-dihydrothieno[3,4-b][1,4]dioxin was dropped slowly, followed by a reaction for 30 minutes, and then 1.0 equivalent of tributyltin chloride was added, followed by a reaction for 1 hour. Moreover, a 1.6 N n-butyl lithium/hexane solution in an amount of 1.1 equivalents relative to 2,3-dihydrothieno[3,4-b][1,4]dioxin was dropped slowly, followed by a reaction for 30 minutes, and then 1.0 equivalent of tributyltin chloride was added, followed by a reaction for 1 hour, and then the reaction was stopped by the addition of an excessive amount of a saturated aqueous sodium chloride solution. The reaction liquid was washed three times with a saturated aqueous sodium chloride solution, then the product was extracted from the resulting reaction liquid to an organic layer using diethyl ether, followed by drying over sodium sulfate, and then the solvent was evaporated, so that 5,7-ditributyltin-2,3-dihydrothieno[3,4-b][1,4]dioxin represented by formula (6c) was obtained.

The result of the $^1$H-NMR measurement of 5,7-ditributyltin-2,3-dihydrothieno[3,4-b][1,4]dioxin is shown below.

$^1$H-NMR (500 MHz, CDCl$_3$, TMS) δ: 4.11 (4H, s), 1.55 (12H, quint.), 1.32 (12H, h), 1.08 (12H, t), 0.92 (18H, t)

To 5,7-ditributyltin-2,3-dihydrothieno[3,4-b][1,4]dioxin represented by formula (6c) were added 2.0 equivalents of 4-bromo-1H-thieno[3,4-d]imidazol-2(3H)-one represented by formula (5a), 5 ml/mol of dry toluene, and 0.2 equivalents of trans-dichlorobistriphenylphosphine palladium, then a reaction was advanced under reflux at 130° C. for 40 hours in an argon gas atmosphere, and then the reaction was stopped by the addition of an excessive saturated aqueous ammonium chloride solution. The product was extracted from the resulting reaction liquid to an organic layer using diethyl ether, followed by drying over sodium sulfate, and then the solvent was evaporated, followed by a purification step by column separation using an ethyl acetate/hexane solvent, so that 4-[7-(2-oxo-2,3-dihydro-1H-thieno[3,4-d]imidazol-4-yl)-2,3-dihydrothieno[3,4-b][1,4]dioxin-5-yl]-1H-thieno[3,4-d]imidazol-2(3H)-one represented by formula (1c) was obtained.

The result of the $^1$H-NMR measurement of 4-[7-(2-oxo-2,3-dihydro-1H-thieno[3,4-d]imidazol-4-yl)-2,3-dihydrothieno[3,4-b][1,4]dioxin-5-yl]-1H-thieno[3,4-d]imidazol-2(3H)-one is shown below.

$^1$H-NMR (500 MHz, CDCl$_3$, TMS) δ: 4.20 (4H, s), 6.34 (2H, s)

The resulting compound represented by formula (1c) was dissolved in a concentration of 0.01M or less in a 0.1 M tetrabutylammonium/acetonitrile solution and then was electrochemically polymerized by the application of a potential at a sweeping rate of 100 mV/sec over the range of from 0 to 1.43 V, so that a film of a polymer represented by formula (2c) was formed. When the electrochromic properties of the resulting film were examined by using a UV-Vis spectrum, it was confirmed that a violet color with an absorbance maximum around 550 nm was developed at the time of coloration (dedoping) and there was no absorbance maximum in the visible range at the time of decoloration (doping).

Example 4

Synthesis of 4-[7-(2-oxo-2,3-dihydro-1H-thieno[3,4-d]imidazol-4-yl)-2,1,3-benzothiadiazol-4-yl]-1H-thieno[3,4-d]imidazol-2(3H)-one represented by formula (1d) and a polymer represented by formula (2d)

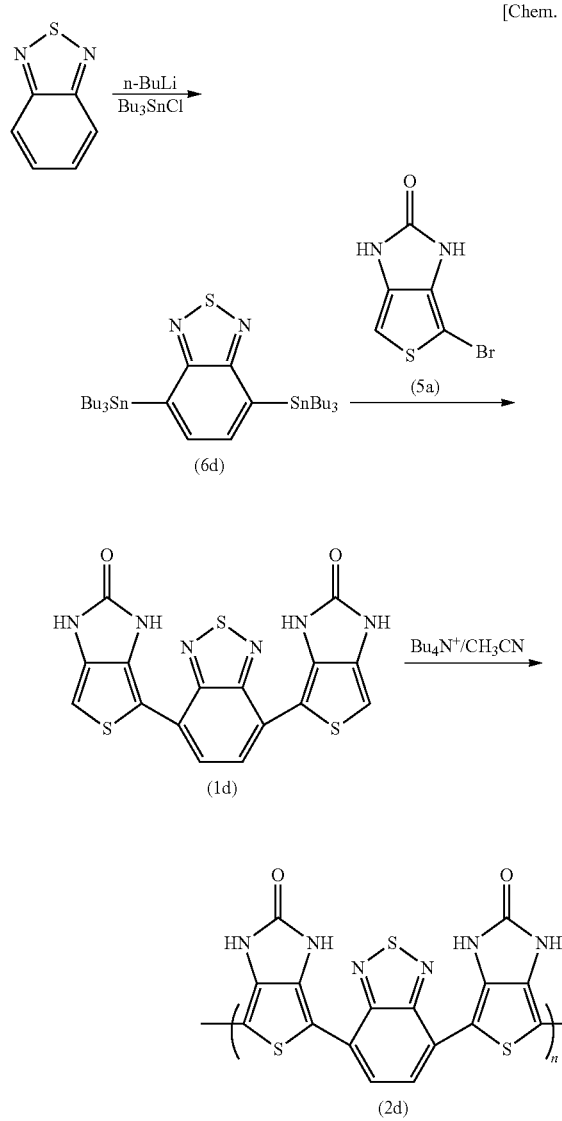

4-Bromo-1H-thieno[3,4-d]imidazol-2(3H)-one represented by formula (5a) was obtained in the same manner as in Example 1. 2,1,3-Benzothiazole was dissolved in 2 ml/mmol of dry tetrahydrofuran and was kept at −78° C. in a dry ice-cooled methanol bath. Under argon gas atmosphere, a 1.6 N n-butyl lithium/hexane solution in an amount of 1.1 equivalents relative to 2,1,3-benzothiazole was dropped slowly, followed by a reaction for 30 minutes, and then 1.0 equivalent of tributyltin chloride was added, followed by a reaction for 1 hour. Moreover, a 1.6 N n-butyl lithium/hexane solution in an amount of 1.1 equivalents relative to 2,1,3-benzothiazole was dropped slowly, followed by a reaction for 30 minutes, and then 1.0 equivalent of tributyltin chloride was added, followed by a reaction for 1 hour, and then the reaction was stopped by the addition of an excessive amount of a saturated aqueous sodium chloride solution. The reaction liquid was washed three times with a saturated aqueous sodium chloride solution, then the product was extracted from the resulting reaction liquid to an organic layer using diethyl ether, followed by drying over sodium sulfate, and then the solvent was evaporated, so that 4,7-ditributyltin-2,1,3-benzothiazole represented by formula (6d) was obtained.

The result of the $^1$H-NMR measurement of 4,7-ditributyltin-2,1,3-benzothiazole is shown below.

$^1$H-NMR (500 MHz, CDCl$_3$, TMS) δ: 8.04 (2H, s), 1.60 (12H, quint.), 1.36 (12H, h), 1.11 (12H, t), 0.91 (18H, t)

To 4,7-ditributyltin-2,1,3-benzothiazole represented by formula (6d) were added 2.0 equivalents of 4-bromo-1H-thieno[3,4-d]imidazol-2(3H)-one represented by formula (5a), 5 ml/mol of dry toluene, and 0.2 equivalents of trans-dichlorobistriphenylphosphine palladium, then a reaction was advanced under reflux at 130° C. for 40 hours in an argon gas atmosphere, and then the reaction was stopped by the addition of an excessive saturated aqueous ammonium chloride solution. The product was extracted from the resulting reaction liquid to an organic layer using diethyl ether, followed by drying over sodium sulfate, and then the solvent was evaporated, followed by a purification step by column separation using an ethyl acetate/hexane solvent, so that 4-[7-(2-oxo-2,3-dihydro-1H-thieno[3,4-d]imidazol-4-yl)-2,1,3-benzothiazol-4-yl]-1H-thieno[3,4-d]imidazol-2(3H)-one represented by formula (1d) was obtained.

The result of the $^1$H-NMR measurement of 4-[7-(2-oxo-2,3-dihydro-1H-thieno[3,4-d]imidazol-4-yl)-2,1,3-benzothiazol-4-yl]-1H-thieno[3,4-d]imidazol-2(3H)-one is shown below.

$^1$H-NMR (500 MHz, CDCl$_3$, TMS) δ: 6.41 (2H, s), 9.92 (2H, s)

The resulting compound represented by formula (1d) was dissolved in a concentration of 0.01M or less in a 0.1 M tetrabutylammonium/acetonitrile solution and then was electrochemically polymerized by the application of a potential at a sweeping rate of 100 mV/sec over the range of from 0 to 1.40 V, so that a film of a polymer represented by formula (2d) was formed. When the electrochromic properties of the resulting film were examined by using a UV-Vis spectrum, it was confirmed that a pale violet color with a broad absorbance maximum around 570 nm was developed at the time of coloration (dedoping) and there was no absorbance maximum in the visible range at the time of decoloration (doping).

Example 5

Synthesis of 4-[4-(1,3-dimethyl-2-oxo-2,3-dihydro-1H-thieno[3,4-d]imidazol-4-yl)phenyl]-1,3-dimethyl-1H-thieno[3,4-d]imidazol-2(3H)-one represented by formula (1e)

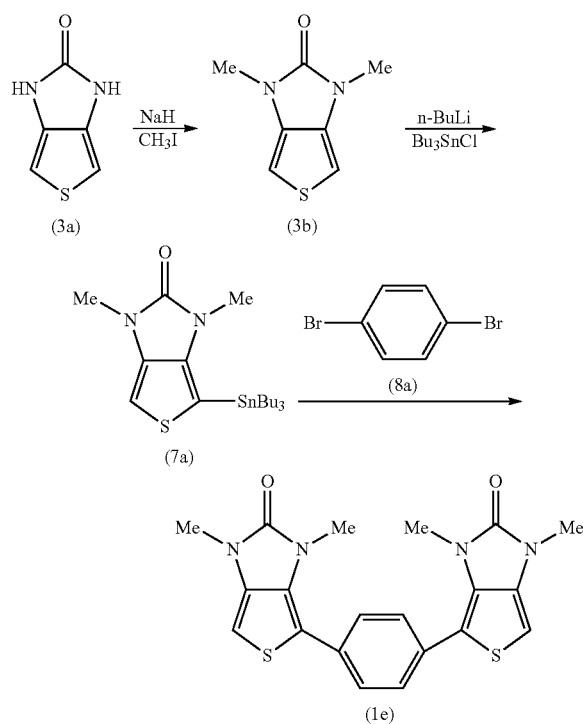

[Chem. 41]

To 1H-thieno[3,4-d]imidazol-2(3H)-one represented by formula (3a) was reacted with 2.2 equivalents of sodium hydride in 3 ml/mmol of tetrahydrofuran for 1 hour under argon gas atmosphere while being kept at 0° C. in an ice bath, and then 2.1 equivalents of methyl iodide was added and a reaction was further done for 12 hours at room temperature. The reaction was stopped by adding an excessive amount of a mixed aqueous solution of ion exchange water:ammonium chloride=3:1. The product was separately extracted from the resulting reaction liquid to an organic layer using diethyl ether and dried over sodium sulfate and then the solvent was evaporated, followed by a purification step by column separation using an ethyl acetate/hexane solvent, so that 1,3-dimethyl-1H-thieno[3,4-d]imidazol-2(3H)-one represented by formula (3b) was obtained.

The result of the $^1$H-NMR measurement of 1,3-dimethyl-1H-thieno[3,4-d]imidazol-2(3H)-one is shown below.

$^1$H-NMR (500 MHz, CDCl$_3$, TMS) δ: 6.27 (2H, s), 3.34 (6H, s)

The resulting 1,3-dimethyl-1H-thieno[3,4-d]imidazol-2(3H)-one represented by formula (3b) was dissolved in 2 ml/mmol of dry tetrahydrofuran and was kept at −78° C. in a dry ice-cooled methanol bath. Under argon gas atmosphere, a 1.6 N n-butyl lithium/hexane solution in an amount of 1.1 equivalents relative to 1,3-dimethyl-1H-thieno[3,4-d]imidazol-2(3H)-one represented by formula (3b) was dropped slowly, followed by a reaction for 30 minutes, and then 1.0 equivalent of tributyltin chloride was added, followed by a reaction for 1 hour, and then the reaction was stopped by the addition of an excessive amount of a saturated aqueous sodium chloride solution. The reaction liquid was washed three times with a saturated aqueous sodium chloride solution, then the product was extracted from the resulting reaction liquid to an organic layer using diethyl ether, followed by drying over sodium sulfate, and then the solvent was evaporated, so that 4-tributyltin-1,3-dimethyl-1H-thieno[3,4-d]imidazol-2(3H)-one represented by formula (7a) was obtained.

The result of the $^1$H-NMR measurement of 4-tributyltin-1,3-dimethyl-1H-thieno[3,4-d]imidazol-2(3H)-one is shown below.

$^1$H-NMR (500 MHz, CDCl$_3$, TMS) δ: 6.28 (1H, s), 3.34 (6H, s), 1.59 (6H, quint.), 1.36 (6H, h), 1.13 (6H, t), 0.91 (9H, t)

To 4-tributyltin-1,3-dimethyl-1H-thieno[3,4-d]imidazol-2(3H)-one represented by formula (7a) were added 0.5 equivalents of 1,4-dibromobenzene represented by formula (8a), 5 ml/mmol of dry toluene, and 0.2 equivalents of trans-dichlorobistriphenylphosphine palladium. Under argon gas atmosphere, a reaction was advanced by refluxing at 130° C. for 40 hours, and then the reaction was stopped by adding an excessive amount of a saturated aqueous ammonium chloride solution. The product was extracted from the resulting reaction liquid to an organic layer using diethyl ether, followed by drying over sodium sulfate, and then the solvent was evaporated, followed by a purification step by column separation using an ethyl acetate/hexane solvent, so that 4-[4-(1,3-dimethyl-2-oxo-2,3-dihydro-1H-thieno[3,4-d]imidazol-4-yl)phenyl]-1,3-dimethyl-1H-thieno[3,4-d]imidazol-2(3H)-one represented by formula (1e) was obtained.

The result of the $^1$H-NMR measurement of 4-[4-(1,3-dimethyl-2-oxo-2,3-dihydro-1H-thieno[3,4-d]imidazol-4-yl)phenyl]-1,3-dimethyl-1H-thieno[3,4-d]imidazol-2(3H)-one is shown below.

$^1$H-NMR (500 MHz, CDCl$_3$, TMS) δ: 6.30 (2H, s), 3.34 (12H, s), 7.44 (4H, s)

Example 6

Synthesis of 4-[4-(1,3-bis(2,2-dimethylpropanoyl)-2-oxo-2,3-dihydro-1H-thieno[3,4-d]imidazol-4-yl)phenyl]-1,3-bis(2,2-dimethylpropanoyl)-1H-thieno[3,4-d]imidazol-2(3H)-one represented by formula (1f)

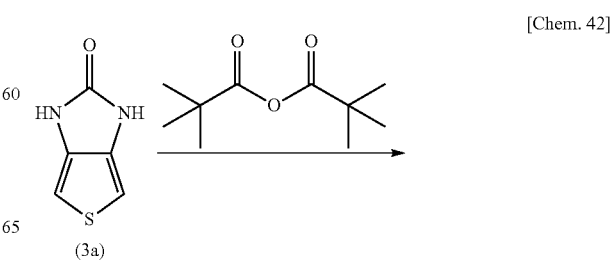

[Chem. 42]

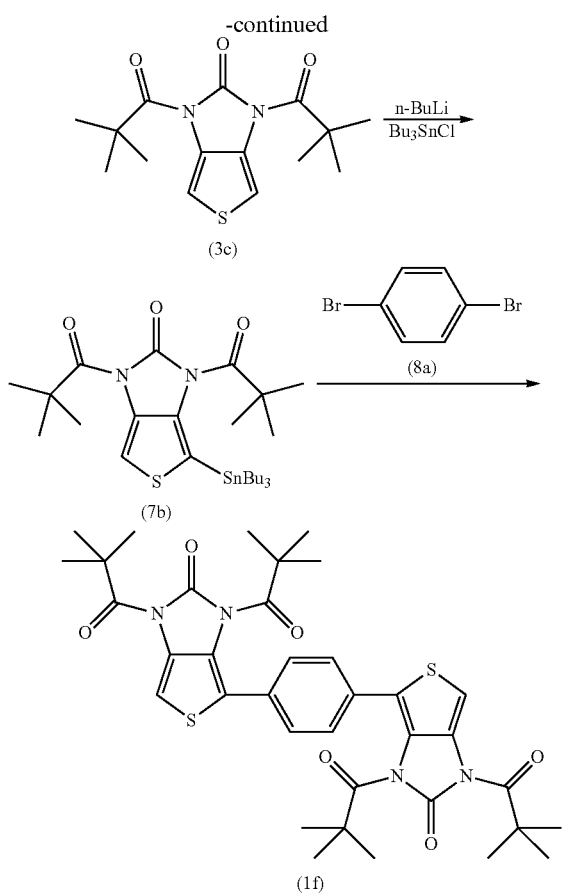

To 1H-thieno[3,4-d]imidazol-2(3H)-one represented by formula (3a) were added 6 ml/mmol of pivalic anhydride and 0.1 equivalents of N,N-dimethyl-4-aminopyridine, and a reaction was performed for one hour under argon gas atmosphere while keeping at 120° C. in an oil bath. The reaction liquid was washed with ion exchange water three times, then the product was extracted to an organic layer using diethyl ether, followed by drying over sodium sulfate, and then the solvent was evaporated. Via a purification step by column separation using an ethyl acetate/hexane solvent, 1,3-bis(2,2-dimethylpropanoyl)-1H-thieno[3,4-d]imidazol-2(3H)-one represented by formula (3c) was obtained.

The result of the $^1$H-NMR measurement of 1,3-bis(2,2-dimethylpropanoyl)-1H-thieno[3,4-d]imidazol-2(3H)-one is shown below.

$^1$H-NMR (500 MHz, CDCl$_3$, TMS) δ: 7.33 (2H, s), 1.49 (18H, s)

The resulting 1,3-bis(2,2-dimethylpropanoyl)-1H-thieno[3,4-d]imidazol-2(3H)-one represented by formula (3c) was dissolved in 2 ml/mmol of dry tetrahydrofuran and was kept at −78° C. in a dry ice-cooled methanol bath. Under argon gas atmosphere, a 1.6 N n-butyl lithium/hexane solution in an amount of 1.1 equivalents relative to 1,3-bis(2,2-dimethylpropanoyl)-1H-thieno[3,4-d]imidazol-2(3H)-one represented by formula (3c) was dropped slowly, followed by a reaction for 30 minutes, and then 1.0 equivalent of tributyltin chloride was added, followed by a reaction for 1 hour, and then the reaction was stopped by the addition of an excessive amount of a saturated aqueous sodium chloride solution. The reaction liquid was washed three times with a saturated aqueous sodium chloride solution, then the product was extracted from the resulting reaction liquid to an organic layer using diethyl ether, followed by drying over sodium sulfate, and then the solvent was evaporated, so that 4-tributyltin-1,3-bis(2,2-dimethylpropanoyl)-1H-thieno[3,4-d]imidazol-2(3H)-one represented by a formula (7b) was obtained.

The result of the $^1$H-NMR measurement of 4-tributyltin-1,3-bis(2,2-dimethylpropanoyl)-1H-thieno[3,4-d]imidazol-2(3H)-one is shown below.

$^1$H-NMR (500 MHz, CDCl$_3$, TMS) δ: 7.10 (1H, s), 1.60 (6H, quint.), 1.50 (18H, s), 1.35 (6H, h), 1.10 (6H, t), 0.91 (9H, t)

To 4-tributyltin-1,3-bis(2,2-dimethylpropanoyl)-1H-thieno[3,4-d]imidazol-2(3H)-one represented by formula (7b) were added 0.5 equivalents of 1,4-dibromobenzene represented by formula (8a), 5 ml/mmol of dry toluene, and 0.2 equivalents of trans-dichlorobistriphenylphosphine palladium. Under argon gas atmosphere, a reaction was advanced by refluxing at 130° C. for 40 hours, and then the reaction was stopped by adding an excessive amount of a saturated aqueous ammonium chloride solution. The product was extracted from the resulting reaction liquid to an organic layer using diethyl ether, followed by drying over sodium sulfate, and then the solvent was evaporated, followed by a purification step by column separation using an ethyl acetate/hexane solvent, so that 4-[4-(1,3-bis(2,2-dimethylpropanoyl)-2-oxo-2,3-dihydro-1H-thieno[3,4-d]imidazol-4-yl)phenyl]-1,3-bis(2,2-dimethylpropanoyl)-1H-thieno[3,4-d]imidazol-2(3H)-one represented by formula (1f) was obtained.

The result of the $^1$H-NMR measurement of 4-[4-(1,3-bis(2,2-dimethylpropanoyl)-2-oxo-2,3-dihydro-1H-thieno[3,4-d]imidazol-4-yl)phenyl]-1,3-bis(2,2-dimethylpropanoyl)-1H-thieno[3,4-d]imidazol-2(3H)-one is shown below.

$^1$H-NMR (500 MHz, CDCl$_3$, TMS) δ: 6.30 (2H, s), 1.50 (36H, s), 7.44 (4H, s)

Production Example 2

Synthesis of tert-butyl 4-[(tert-butoxycarbonyl)amino]thien-3-ylcarbamate

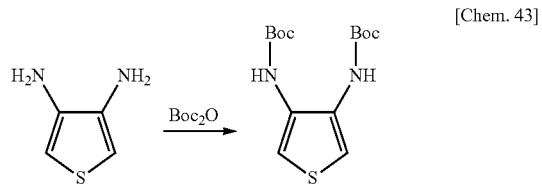 [SMILES: "Boc2O" ; Nc1cscc1N ; CC(C)(C)OC(=O)Nc1cscc1NC(=O)OC(C)(C)C]

[Chem. 43]

The 3,4-diaminothiophene obtained in Production Example 1 was dissolved in tetrahydrofuran in an amount equivalent to 3 ml/mmol, and to this was dropped slowly di-tert-butyl dicarbonate in an amount of 2.5 equivalents relative to 3,4-diaminothiophene. After the dropping, stirring was further done for 8 hours and then tetrahydrofuran and so on were distilled off, and the residue was purified by silica gel column chromatography using an ethyl acetate/hexane solvent, so that tert-butyl 4-[(tert-butoxycarbonyl)amino]thien-3-ylcarbamate was obtained. The yield based on 3,4-diaminothiophene was 95%.

The result of the ¹H-NMR measurement of tert-butyl 4-[(tert-butoxycarbonyl)amino]thien-3-ylcarbamate is shown below.

¹H-NMR (500 MHz, CDCl₃, TMS) δ: 7.15 (2H, s), 6.66 (2H, s), 1.51 (18H, s)

Example 7

Synthesis of tert-butyl 4-tributyltin-2,3-dihydro-2-oxo-1H-thieno[3,4-d]imidazole-1-carboxylate

[Chem. 44]

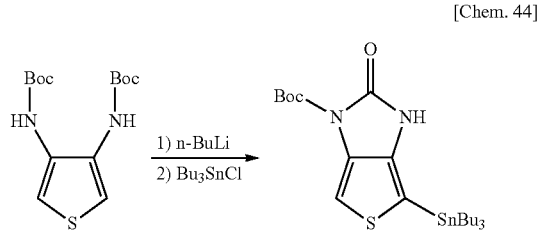

The tert-butyl 4-[(tert-butoxycarbonyl)amino]thien-3-ylcarbamate obtained in Production Example 2 was dissolved in tetrahydrofuran in an amount equivalent to 40 ml/mmol and kept at −78° C. in a dry ice-cooled methanol bath. To this was dropped a 1.6 N n-butyl lithium/hexane solution in an amount of 3.5 equivalents relative to tert-butyl 4-[(tert-butoxycarbonyl)amino]thien-3-ylcarbamate under argon gas atmosphere, and after the dropping a reaction was further performed for 30 minutes and then the temperature was increased to −20° C. Then, tributyltin chloride was added in an amount of 1.05 equivalents relative to tert-butyl 4-[(tert-butoxycarbonyl)amino]thien-3-ylcarbamate, and a reaction was performed at −20° C. for 1 hour under stirring, and then the temperature was increased to 25° C. Then, a reaction was performed for 1 hour under stirring, and then the reaction was stopped by adding an excessive amount of saturated brine. The reaction liquid was thoroughly washed with saturated brine, and then the organic layer was taken and the solvent was distilled off, so that tert-butyl 4-tributyltin-2,3-dihydro-2-oxo-1H-thieno[3,4-d]imidazole-1-carboxylate was obtained. The yield based on tert-butyl 4-[(tert-butoxycarbonyl)amino]thien-3-ylcarbamate was 80%.

The result of the ¹H-NMR measurement of tert-butyl 4-tributyltin-2,3-dihydro-2-oxo-1H-thieno[3,4-d]imidazole-1-carboxylate is shown below.

¹H-NMR (500 MHz, CDCl₃, TMS) δ: 7.10 (1H, s), 1.65 (9H, s), 1.57 (6H, quint.), 1.31 (6H, h), 1.12 (6H, t), 0.91 (9H, t)

Synthesis of 4-(2,3-dihydro-2-oxo-1H-thieno[3,4-d]imidazol-4-yl)phenyl]-2,3-dihydro-1H-thieno[3,4-d]imidazol-2-one

[Chem. 45]

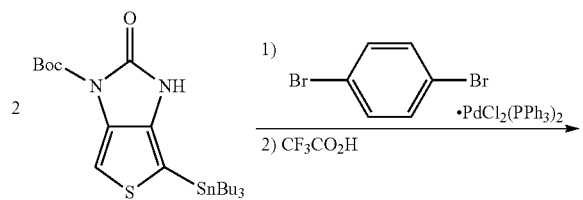

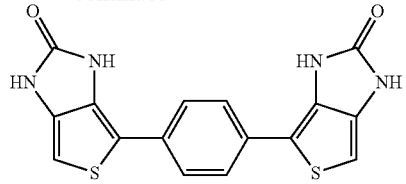

To 1,4-dibromobenzene were added 2.0 equivalents of tert-butyl 4-tributyltin-2,3-dihydro-2-oxo-1H-thieno[3,4-d]imidazole-1-carboxylate, dry 1,4-dioxane in an amount equivalent to 10 ml/mmol relative to 1,4-dibromobenzene, and 0.1 equivalents of trans-dichlorobistriphenylphosphine palladium. Under argon gas atmosphere, a reaction was advanced by refluxing at 120° C. for 40 hours, and then the reaction was stopped by adding an excessive amount of a saturated aqueous ammonium chloride solution. The resulting reaction liquid was filtered while being diluted with ethyl acetate, and to the resulting filtrate was added three-fold volume of a saturated aqueous potassium fluoride solution, followed by stirring for 2 hours. After the removal of the aqueous phase and insoluble matter, the organic layer containing the product was dried over sodium sulfate, then the solvent was distilled off, and the residue was purified by silica gel column chromatography using an ethyl acetate/hexane solvent, so that tert-butyl 4-[4-(2,3-dihydro-2-oxo-1-tert-butoxycarbonyl-1H-thieno[3,4-d]imidazol-4-yl)phenyl]-2,3-dihydro-2-oxo-1H-thieno[3,4-d]imidazole-1-carboxylate was obtained.

Trifluoroacetic acid in an amount of 40 equivalents relative to the obtained tert-butyl 4-[4-(2,3-dihydro-2-oxo-1-tert-butoxycarbonyl-1H-thieno[3,4-d]imidazol-4-yl)phenyl]-2,3-dihydro-2-oxo-1H-thieno[3,4-d]imidazole-1-carboxylate was added and a reaction was carried out at 25° C. for 3 hours. The resulting reaction liquid was dropped slowly to a saturated aqueous sodium carbonate solution to neutralize, thereby stopping the reaction. Ethyl acetate was added to the reaction liquid and stirred, and then an organic layer was taken and the solvent was distilled off. The residue was purified by silica gel column chromatography using an ethyl acetate/hexane solvent, so that 4-[4-(2,3-dihydro-2-oxo-1H-thieno[3,4-d]imidazol-4-yl)phenyl]-2,3-dihydro-1H-thieno[3,4-d]imidazol-2-one was obtained. The yield based on the charged tert-butyl 4-[4-(2,3-dihydro-2-oxo-1-tert-butoxycarbonyl-1H-thieno[3,4-d]imidazol-4-yl)phenyl]-2,3-dihydro-2-oxo-1H-thieno[3,4-d]imidazole-1-carboxylate was 90%.

[Evaluation of the Electrochromic Properties of a Polymer]

The resulting 4-[4-(2,3-dihydro-2-oxo-1H-thieno[3,4-d]imidazol-4-yl)phenyl]-2,3-dihydro-1H-thieno[3,4-d]imidazol-2-one was dissolved in a concentration of 0.005 M in a 0.1 M tetrabutylammonium perchlorate/propylene carbonate solution, and was electrochemically polymerized by applying a voltage at a sweeping rate of 100 mV/sec over the range of from 0 to 1.30 V using an ITO electrode (anode) from GEOMATEC Corp. and a platinum electrode (cathode) from The Nilaco Corp., so that a film of a polymer composed of that compound was formed on the ITO electrode (anode). Then, the voltage was brought to 0 V from the state where a voltage was applied to the ITO electrode (anode). This time was defined as a time of coloration (a time of dedoping). Moreover, the time when a voltage of 1.3 V was applied to the ITO electrode (anode) was defined as a time of decoloration (a time of doping). When the electrochromic properties of the polymer were examined by measuring a UV-Vis spectrum (ultraviolet-visible absorption spectrum) at a time of coloration and at a time of decoloration, it was confirmed that an M color with an absorbance maximum around 500 nm was developed at the time of coloration (dedoping) and there was no absorbance maximum in a visible light range at the time of decoloration (doping).

Example 8

Synthesis of 4-[9-methyl-6-(2,3-dihydro-2-oxo-1H-thieno[3,4-d]imidazol-4-yl)-9H-carbazol-3-yl]-2,3-dihydro-1H-thieno[3,4-d]imidazol-2-one

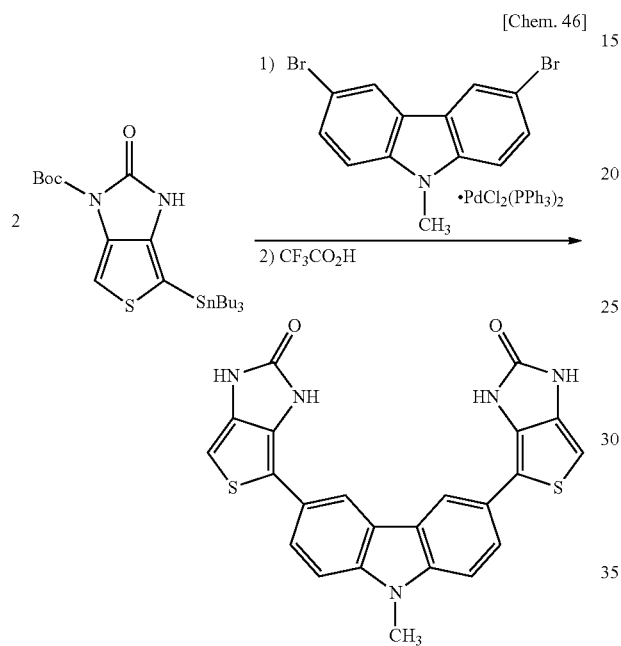

To 3,6-dibromo-9-methyl-9H-carbazole were added 2.0 equivalents of tert-butyl 4-tributyltin-2,3-dihydro-2-oxo-1H-thieno[3,4-d]imidazole-1-carboxylate obtained in the same manner as described in Example 1, dry 1,4-dioxane in an amount equivalent to 10 ml/mol relative to 3,6-dibromo-9-methyl-9H-carbazole, and 0.1 equivalents of trans-dichloro-bistriphenylphosphine palladium. Under argon gas atmosphere, a reaction was advanced by refluxing at 120° C. for 40 hours, and then the reaction was stopped by adding an excessive amount of a saturated aqueous ammonium chloride solution. The resulting reaction liquid was filtered while being diluted with ethyl acetate, and to the resulting filtrate was added three-fold volume of a saturated aqueous potassium fluoride solution, followed by stirring for 2 hours. After the removal of the aqueous phase and insoluble matter, the organic layer containing the product was dried over sodium sulfate, then the solvent was distilled off, and the residue was purified by silica gel column chromatography using an ethyl acetate/hexane solvent, so that tert-butyl 4-[9-methyl-6-(2,3-dihydro-2-oxo-1-tert-butoxycarbonyl-1H-thieno[3,4-d]imidazol-4-yl)-9H-carbazol-3-yl]-2,3-dihydro-2-oxo-1H-thieno[3,4-d]imidazole-1-carboxylate was obtained.

Trifluoroacetic acid in an amount of 40 equivalents was added to the obtained tert-butyl 4-[9-methyl-6-(2,3-dihydro-2-oxo-1-tert-butoxycarbonyl-1H-thieno[3,4-d]imidazol-4-yl)-9H-carbazol-3-yl]-2,3-dihydro-2-oxo-1H-thieno[3,4-d] imidazole-1-carboxylate and a reaction was carried out at 25° C. for 3 hours. The resulting reaction liquid was dropped slowly to a saturated aqueous sodium carbonate solution to neutralize, thereby stopping the reaction. Ethyl acetate was added to the reaction liquid and stirred, and then an organic layer was taken and the solvent was distilled off. The residue was purified by silica gel column chromatography using an ethyl acetate/hexane solvent, so that 4-[9-methyl-6-(2,3-dihydro-2-oxo-1H-thieno[3,4-d]imidazol-4-yl)-9H-carbazol-3-yl]-2,3-dihydro-1H-thieno[3,4-d]imidazol-2-one was obtained. The yield based on the charged tert-butyl 4-[9-methyl-6-(2,3-dihydro-2-oxo-1-tert-butoxycarbonyl-1H-thieno[3,4-d]imidazol-4-yl)-9H-carbazol 3-yl]-2,3-dihydro-2-oxo-1H-thieno[3,4-d]imidazole-1-carboxy late was 90%.

[Evaluation of the Electrochromic Properties of a Polymer]

Using the resulting 4-[9-methyl-6-(2,3-dihydro-2-oxo-1H-thieno[3,4-d]imidazol-4-yl)-9H-carbazol-3-yl]-2,3-dihydro-1H-thieno[3,4-d]imidazol-2-one, the electrochromic properties of the polymer composed thereof were evaluated by the same way as Example 7. It was confirmed that the polymer developed a Y color having an absorption maximum near 400 nm at the time of coloration (dedoping) and had no absorption maximum in a visible light range at the time of decoloration (doping).

Example 9

Synthesis of 4-[7-(2,3-dihydro-2-oxo-1H-thieno[3,4-d]imidazol-4-yl)-2,3-dihydrothieno[3,4-b]-1,4-dioxin-5-yl]-2,3-dihydro-1H-thieno[3,4-d]imidazol-2-one

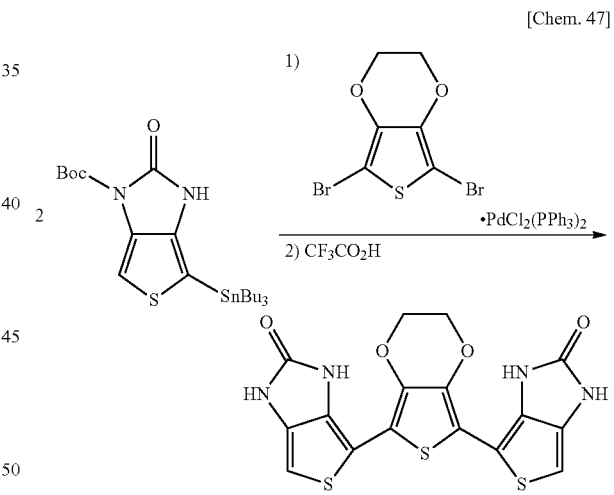

To 5,7-dibromo-2,3-dihydrothieno[3,4-b]-1,4-dioxin were added 2.0 equivalents of tert-butyl 4-tributyltin-2,3-dihydro-2-oxo-1H-thieno[3,4-d]imidazole-1-carboxylate obtained in the same manner as described in Example 7, dry 1,4-dioxane in an amount equivalent to 10 ml/mol relative to 5,7-dibromo-2,3-dihydrothieno[3,4-b]-1,4-dioxin, and 0.1 equivalents of trans-dichlorobistriphenylphosphine palladium. Under argon gas atmosphere, a reaction was advanced by refluxing at 120° C. for 40 hours, and then the reaction was stopped by adding an excessive amount of a saturated aqueous ammonium chloride solution. The resulting reaction liquid was filtered while being diluted with ethyl acetate, and to the resulting filtrate was added three-fold volume of a saturated aqueous potassium fluoride solution, followed by stirring for 2 hours. After the removal of the aqueous phase and insoluble matter, the organic layer containing the product was dried over sodium sulfate, then the solvent was distilled off, and the residue was purified by silica gel column chromatography using an ethyl acetate/hexane solvent, so that tert-butyl 4-[7-(2,3-dihydro-2-oxo-1-tert-butoxycarbonyl-1H-thieno[3,4-d]imidazol-4-yl)-2,3-dihydrothieno[3,4-b]-1,4-dioxin-5-yl]-2,3-dihydro-2-oxo-1H-thieno[3,4-d]imidazole-1-carboxylate was obtained.

To the obtained tert-butyl 4-[7-(2,3-dihydro-2-oxo-1-tert-butoxycarbonyl-1H-thieno[3,4-d]imidazol-4-yl)-2,3-dihydrothieno[3,4-b]-1,4-dioxin-5-yl]-2,3-dihydro-2-oxo-1H-thieno[3,4-d]imidazole-1-carboxylate was added 40 equivalents of trifluoroacetic acid, and then a reaction was performed at 25° C. for 3 hours. The resulting reaction liquid was dropped slowly to a saturated aqueous sodium carbonate solution to neutralize, thereby stopping the reaction. Ethyl acetate was added to the reaction liquid and stirred, and then an organic layer was taken and the solvent was distilled off. The residue was purified by silica gel column chromatography using an ethyl acetate/hexane solvent, so that 4-[7-(2,3-dihydro-2-oxo-1H-thieno[3,4-d]imidazol-4-yl)-2,3-dihydrothieno[3,4-b]-1,4-dioxin-5-yl]-2,3-dihydro-1H-thieno[3,4-d]imidazol-2-one was obtained. The yield based on the charged tert-butyl 4-[7-(2,3-dihydro-2-oxo-1-tert-butoxycarbonyl-1H-thieno[3,4-d]imidazol-4-yl)-2,3-dihydrothieno[3,4-b]-1,4-dioxin-5-yl]-2,3-dihydro-2-oxo-1H-thieno[3,4-d]imidazole-1-carboxylate was 90%.

[Evaluation of the Electrochromic Properties of a Polymer]

Using the resulting 4-[7-(2,3-dihydro-2-oxo-1H-thieno[3,4-d]imidazol-4-yl)-2,3-dihydrothieno[3,4-b]-1,4-dioxin-5-yl]-2,3-dihydro-1H-thieno[3,4-d]imidazol-2-one, the electrochromic properties of the polymer composed thereof were evaluated by the same way as Example 7. It was confirmed that the polymer was in a violet color having an absorption maximum near 550 nm at the time of coloration (dedoping) and had no absorption maximum in the visible range at the time of decoloration (doping).

Example 10

Synthesis of tert-butyl 2-tributyltin-4-[(tert-butoxycarbonyl)amino]thien-3-ylcarbamate

[Chem. 48]

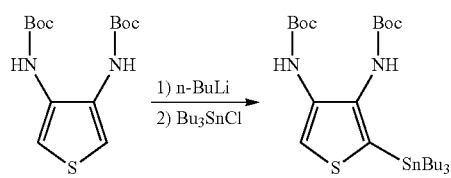

The tert-butyl 4-[(tert-butoxycarbonyl)amino]thien-3-ylcarbamate obtained in Production Example 2 was dissolved in tetrahydrofuran in an amount equivalent to 40 ml/mmol and kept at −78° C. in a dry ice-cooled methanol bath. To this was dropped a 1.6 N n-butyl lithium/hexane solution in an amount of 3.5 equivalents relative to tert-butyl 4-[(tert-butoxycarbonyl)amino]thien-3-ylcarbamate under argon gas atmosphere, and after the dropping a reaction was further performed for 30 minutes and then the temperature was increased to −20° C. Then, tributyltin chloride was added in an amount of 1.05 equivalents relative to tert-butyl 4-[(tert-butoxycarbonyl)amino]thien-3-ylcarbamate, and a reaction was performed at −20° C. for 1 hour under stirring, and then the reaction was stopped by adding an excessive amount of saturated brine. The reaction liquid was thoroughly washed with saturated brine, and then the organic layer was taken and the solvent was distilled off, so that tert-butyl 2-tributyltin-4-[(tert-butoxycarbonyl)amino]thien-3-ylcarbamate was obtained. The yield based on tert-butyl 4-[(tert-butoxycarbonyl)amino]thien-3-ylcarbamate was 80%.

The result of the $^1$H-NMR measurement of tert-butyl 2-tributyltin-4-[(tert-butoxycarbonyl)amino]thien-3-ylcarbamate is shown below.

$^1$H-NMR (500 MHz, CDCl$_3$, TMS) δ: 7.58 (1H, s), 6.93 (1H, s), 6.02 (1H, s), 1.51 (18H, s), 1.57 (6H, quint.), 1.31 (6H, h), 1.12 (6H, t), 0.91 (9H, t)

Synthesis of 4-[4-(2,3-dihydro-2-oxo-1H-thieno[3,4-d]imidazol-4-yl)phenyl]-2,3-dihydro-1H-thieno[3,4-d]imidazol-2-one

[Chem. 49]

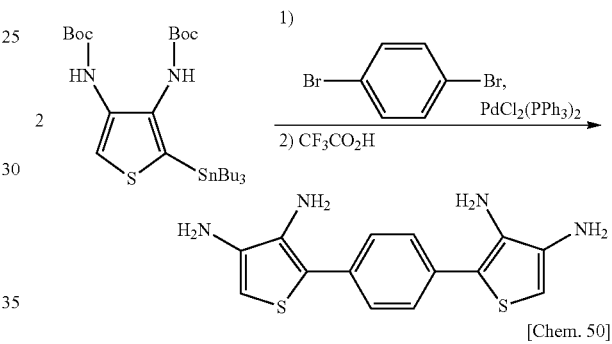

[Chem. 50]

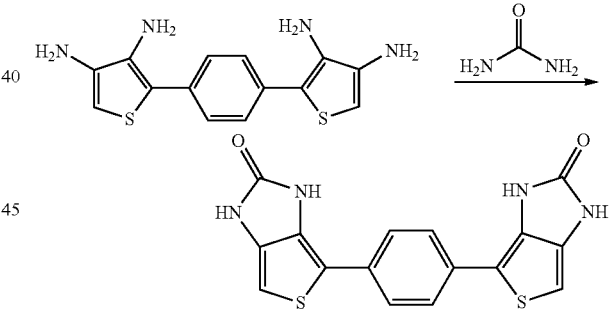

To 1,4-dibromobenzene were added 2.0 equivalents of tert-butyl 2-tributyltin-4-[(tert-butoxycarbonyl)amino]thien-3-ylcarbamate, dry 1,4-dioxane in an amount equivalent to 10 ml/mmol relative to 1,4-dibromobenzene, and 0.1 equivalents of trans-dichlorobistriphenylphosphine palladium. Under argon gas atmosphere, a reaction was advanced by refluxing at 120° C. for 40 hours, and then the reaction was stopped by adding an excessive amount of a saturated aqueous ammonium chloride solution. The resulting reaction liquid was filtered while being diluted with ethyl acetate, and to the resulting filtrate was added three-fold volume of a saturated aqueous potassium fluoride solution, followed by stirring for 2 hours. After the removal of the aqueous phase and insoluble matter, the organic layer containing the product was dried over sodium sulfate, then the solvent was distilled off, and the residue was purified by silica gel column chromatography using an ethyl acetate/hexane solvent, so that tert-butyl 2-[4-

(3,4-bis(tert-butoxycarbonylamino)thien-2-yl)phenyl]-4-tert-butoxycarbonylaminothien-3-ylcarbamate was obtained.

To the resulting tert-butyl 2-[4-(3,4-bis(tert-butoxycarbonylamino)thien-2-yl)phenyl]-4-tert-butoxycarbonylaminothien-3-ylcarbamate was added 80 equivalents of trifluoroacetic acid, and a reaction was performed at 25° C. for 3 hours. The resulting reaction liquid was dropped slowly to a saturated aqueous sodium carbonate solution to neutralize, thereby stopping the reaction. Ethyl acetate was added to the reaction liquid and stirred, and then the organic layer was taken and the solvent was distilled off, and the residue was purified by silica gel column chromatography using an ethyl acetate/hexane solvent, so that 2-[4-(3,4-diaminothien-2-yl)phenyl]thiophene-3,4-diamine was obtained. The yield based on the charged tert-butyl 2-[4-(3,4-bis(tert-butoxycarbonylamino)thien-2-yl)phenyl]-4-tert-butoxycarbonylaminothien-3-ylcarbamate was 90%.

To the resulting 2-[4-(3,4-diaminothien-2-yl)phenyl]thiophene-3,4-diamine were added 2.2 equivalents of urea and amyl alcohol in an amount equivalent to 10 ml/mmol, and under argon gas atmosphere, a reaction was advanced by refluxing at 130° C. for 5 hours, then amyl alcohol was distilled off and the residue was purified by silica gel column chromatography using an ethyl acetate/hexane solvent, so that 4-[4-(2,3-dihydro-2-oxo-1H-thieno[3,4-d]imidazol-4-yl)phenyl]-2,3-dihydro-1H-thieno[3,4-d]imidazol-2-one was obtained. The yield based on 2-[4-(3,4-diaminothien-2-yl)phenyl]thiophene-3,4-diamine was 60%.

Comparative Example 1

1H-thieno[3,4-d]imidazol-2(3H)-one represented by formula (3a) was dissolved in 10 ml/mmol of tetrahydrofuran and was kept at −78° C. in a dry ice-cooled methanol bath. To this was dropped slowly 1.1 N N-bromosuccinic imide dissolved in tetrahydrofuran of an amount of 5 ml/mmol relative to the 1H-thieno[3,4-d]imidazol-2(3H)-one represented by formula (3a), followed by a reaction for 30 minutes, and then the reaction was stopped by adding an excessive amount of a saturated aqueous sodium chloride solution. The product was separately extracted from this reaction liquid to an organic layer using diethyl ether, followed by drying over sodium sulfate, and then the solvent was evaporated. Despite the execution of a purification step by column separation using an ethyl acetate/hexane solvent, the product was a mixture of 4,6-dibromo-1H-thieno[3,4-d]imidazol-2(3H)-one represented by formula (4a) and unreacted 1H-thieno[3,4-d]imidazol-2(3H)-one represented by formula (3a). This fact shows that 4-bromo-1H-thieno[3,4-d]imidazol-2(3H)-one represented by formula (5a) can be obtained by the execution of reactions 1 and 2 in which 1H-thieno[3,4-d]imidazol-2(3H)-one represented by formula (3a) is halogenated and then lithiated and subsequently an acid is added.

Comparative Example 2

1H-thieno[3,4-d]imidazol-2(3H)-one represented by formula (3a) was dissolved in 2 ml/mmol of dry tetrahydrofuran and was kept at −78° C. in a dry ice-cooled methanol bath. Under argon gas atmosphere, a 1.6 N n-butyl lithium/hexane solution in an amount of 1.1 equivalents relative to 1H-thieno[3,4-d]imidazol-2(3H)-one represented by formula (3a) was dropped slowly, followed by a reaction for 30 minutes, and then 1.0 equivalent of tributyltin chloride was added, followed by a reaction for 1 hour, and then the reaction was stopped by the addition of an excessive amount of a saturated aqueous sodium chloride solution. The reaction liquid was washed three times with a saturated aqueous sodium chloride solution, then the product was extracted from the resulting reaction liquid to an organic layer using diethyl ether, followed by drying over sodium sulfate, and then the solvent was evaporated, so that the product was obtained. The product was not the desired 4-tributyltin-1H-thieno[3,4-d]imidazol-2(3H)-one but a mixture of 1-tributyltin-1H-thieno[3,4-d]imidazol-2(3H)-one and a compound in which a fused ring state had been broken due to ring opening. This fact shows that a compound represented by formula (7) is obtained by performing reaction 4 in which a compound represented by formula (3) in which Z is not a hydrogen atom is reacted with a base.

Comparative Example 3

Synthesis of 1H-thieno[3,4-d]imidazol-2(3H)-one

[Chem. 51]

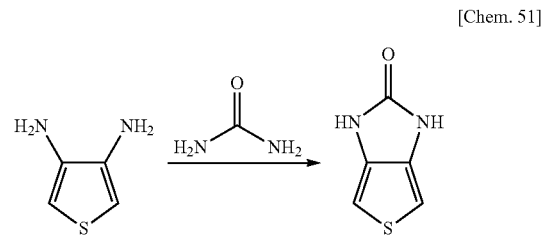

To the 3,4-diaminothiophene obtained in Production Example 1 were added 1.1 equivalents of urea and amyl alcohol in an amount equivalent to 10 ml/mmol, and under argon gas atmosphere, a reaction was advanced by refluxing at 130° C. for 5 hours, then amyl alcohol was distilled off and the residue was purified by silica gel column chromatography using an ethyl acetate/hexane solvent, so that 1H-thieno[3,4-d]imidazol-2(3H)-one was obtained. The yield based on 3,4-diaminothiophene was 55%.

Attempt to synthesize di-tert-butyl 2,3-dihydro-2-oxo-4-tributyltin-1H-thieno[3,4-d]imidazole-1,3-dicarboxylate To the resulting 1H-thieno[3,4-d]imidazol-2(3H)-one were added 2.5 equivalents of di-tert-butyl dicarbonate, 2.5 equivalents of N,N-dimethyl-4-aminopyridine, and dry tetrahydrofuran in an amount equivalent to 5 ml/mmol, and a reaction was advanced under reflux at 80° C. for 5 hours, and then tetrahydrofuran and so on were distilled off, followed by a purification step by column separation using an ethyl acetate/hexane solvent, so that di-tert-butyl 2,3-dihydro-2-oxo-1H-thieno[3,4-d]imidazole-1,3-dicarboxylate represented by formula (9) was obtained. The yield based on 1H-thieno[3,4-d]imidazol-2(3H)-one was 50%.

[Chem. 52]

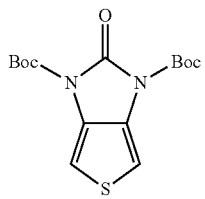

(16)

The resulting di-tert-butyl 2,3-dihydro-2-oxo-1H-thieno[3,4-d]imidazole-1,3-dicarboxylate represented by formula (16) described above was dissolved in dry tetrahydrofuran in an amount equivalent to 2 ml/mmol and kept at −78° C. in a dry ice-cooled methanol bath. To this was slowly dropped a 1.6 N n-butyl lithium/hexane solution in an amount of 1.1 equivalents relative to di-tert-butyl 2,3-dihydro-2-oxo-1H-thieno[3,4-d]imidazole-1,3-dicarboxylate under argon gas atmosphere, and after the dropping a reaction was further performed for 30 minutes. Then, tributyltin chloride was added in an amount of 1.0 equivalent relative to di-tert-butyl 2,3-dihydro-2-oxo-1H-thieno[3,4-d]imidazole-1,3-dicarboxylate, and a reaction was performed for 1 hour, and then the reaction was stopped by adding an excessive amount of saturated brine. The reaction liquid was washed with saturated brine three times, then the resulting organic layer was dried over sodium sulfate and then the solvent was distilled off, so that a product was obtained. The product was not the desired di-tert-butyl 2,3-dihydro-2-oxo-4-tributyltin-1H-thieno[3,4-d]imidazole-1,3-dicarboxylate but a mixture of compounds resulting from breakage of a fused ring state due to ring opening.

This fact shows that even if two amino groups constituting an urea group in 1H-thieno[3,4-d]imidazol-2(3H)-one are protected with organic oxycarbonyl groups such as tert-butoxycarbonyl groups, followed by lithiation of an α-proton of the thiophene ring with n-butyl lithium, and then transmetallation is attempted, it is difficult to obtain the desired di-tert-butyl 2,3-dihydro-2-oxo-4-tributyltin-1H-thieno[3,4-d]imidazole-1,3-dicarboxylate.

Comparative Example 4

The 1H-thieno[3,4-d]imidazol-2(3H)-one and the 2,3-dihydrothieno[3,4-b]-1,4-dioxin both obtained above were mixed in a molar ratio of 1:1, and the mixture was dissolved in a concentration of 0.01M in a 0.1 M tetrabutylammonium perchlorate/propylene carbonate solution, so that monomer-containing electrolytic solution A was prepared. Separately, 4-[7-(2,3-dihydro-2-oxo-1H-thieno[3,4-d]imidazol-4-yl)-2,3-dihydrothieno[3,4-b]-1,4-dioxin-5-yl]-2,3-dihydro-1H-thieno[3,4-d]imidazol-2-one was dissolved in a concentration of 0.01 M in a 0.1 M tetrabutylammonium perchlorate/propylene carbonate solution, so that monomer-containing electrolytic solution B was prepared.

Using these solutions, an ITO electrode (anode) from GEOMATEC Corp., and a platinum electrode (cathode) from The Nilaco Corp., polymerization was performed electrochemically by applying an electric current for one minute at any potential of 0 V, 0.5 V, 1.0 V, and 1.5 V, so that a film of a polymer composed of that compound was formed on the ITO electrode (anode). Then, the voltage was brought to −0.5 V from the state where a voltage was applied to the ITO electrode (anode). This time was defined as a time of coloration (a time of dedoping). Moreover, the time when a voltage of 1.3 V was applied to the ITO electrode (anode) was defined as a time of decoloration (a time of doping). The electrochromic properties of the polymer were visually evaluated at the time of coloration and decoloration. The results are shown in Table 1.

TABLE 1

| | Monomer-containing electrolytic solution A | | | Monomer-containing electrolytic solution B | | |
|---|---|---|---|---|---|---|
| | Film formation | Time of coloration | Time of decoloration | Film formation | Time of coloration | Time of decoloration |
| 0 V | a | Navy blue | Pale blue | b | — | — |
| 0.5 V | a | Bluish violet | Pale blue | b | — | — |
| 1.0 V | a | Violet | Pale gray | a | Violet | Pale gray |
| 1.5 V | a | Violet | Pale gray | a | Violet | Pale gray | a-A polymer was formed on ITO.
b-No polymer was formed on ITO or a polymer was too thin to be visually observed.

As shown in Table 1 above, there was a difference between monomer-containing electrolytic solutions A and B with respect to the colors developed at a time of coloration and a time of decoloration due to the difference in the potential at which polymerization is performed electrochemically. This is probably because in the case of monomer-containing electrolytic solution A, polymerization was carried out using a mixed solution of 1H-thieno[3,4-d]imidazol-2(3H)-one (hereinafter, abbreviated to T) and 2,3-dihydrothieno[3,4-b]-1,4-dioxin (hereinafter, abbreviated to E) and, therefore, T and E differ in an initial polymerization potential, so that the composition of the electrochemically polymerized films differed. Specifically, for example, it is highly probable that there is a repeating pattern of T-E-T-E . . . and repeating patterns of T-E-E-T . . . , T-E-E-E-T . . . , and so on have also been formed. Thus, electrochemical polymerization of a mixture of different monomers like monomer-containing electrolytic solution A is difficult to be controlled because the color tone of a formed film greatly varies depending on the polymerization potential applied during film formation, and is, therefore, unsuitable as an EC material. On the other hand, in the case of using monomer-containing electrolytic solution B, specifically, for example, a monomer unit having been controlled like T-E-T, no change in color tone due to a polymerization potential is observed and the polymer is very suitable as an EC material. In the case of a mixture of different monomers like monomer-containing electrolytic solution A, the combination with T must be a polymerizable unit like E; however, in the case of using monomer-containing electrolytic solution B, specifically, for example, a monomer unit having been controlled like T-E-T, a unit used for the adjustment of color tone can be selected from a wider range because of the absence of the necessity that the moiety E is solely polymerizable and, also in this respect, it is very suitable as an EC material.

The invention claimed is:

1. A π-electron conjugated compound of formula (1):

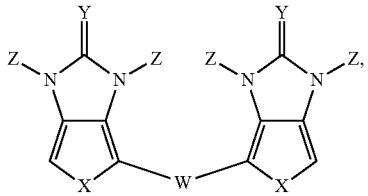

(1)

wherein:
each X is independently an oxygen atom, a sulfur atom, —NH—, or —NR$^1$— (wherein R$^1$ is an optionally substituted alkyl group comprising 1 to 20 carbon atoms or an optionally substituted aryl group comprising 6 to 20 carbon atoms);
each Y is independently an oxygen atom or a sulfur atom;
each Z is independently a hydrogen atom or optionally substituted organic group comprising 1 to 20 carbon atoms; and
W is an ethynylene group, an optionally substituted ethenylene group, an optionally substituted arylene group, or an optionally substituted divalent heteroaromatic ring group.

2. A π-electron conjugated polymer comprising a constitutional unit of formula (2):

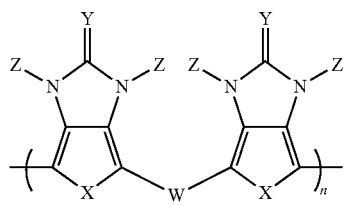

(2)

wherein:
each X is independently an oxygen atom, a sulfur atom, —NH—, or —NR$^1$—, wherein R$^1$ is an optionally substituted alkyl group comprising 1 to 20 carbon atoms or an optionally substituted aryl group having 6 to 20 carbon atoms;
each Y is independently an oxygen atom or a sulfur atom;
each Z is independently a hydrogen atom or an optionally substituted organic groups comprising 1 to 20 carbon atoms;
W is an ethynylene group, an optionally substituted ethenylene group, an optionally substituted arylene group, or a optionally substituted divalent heteroaromatic ring group selected from the group consisting of an N-alkylcarbazole, pyrimidine, pyridazine, triazine, pyrazine, quinoline, purine, a 3-alkylfuran, an N-alkylpyrrole, ethylene-3,4-dioxypyrrole, propylene-3,4-dioxypyrrole, thiophenevinylene, an alkylthiophene, ethylene-3,4-dioxythiophene, propylene-3,4-dioxythiophene, thienofuran, thienopyrazine, isothianaphthene, oxadiazole, selenophene, tellurophene, imidazole, oxazole, thiazole, pyrazole, isoxazole, isothiazole, benzotriazole, pyrane, benzothiadiazole, and benzoxadiazole; and
n is an integer of 2 or greater.

3. An electrochromic material, comprising a π-electron conjugated polymer of claim 2.

4. A method for producing a π-electron conjugated compound of claim 1, the method comprising:
(A) halogenating a compound formula (3):

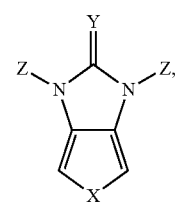

(3)

wherein X, Y, and Z are defined in claim 1, to obtain a compound of formula (4):

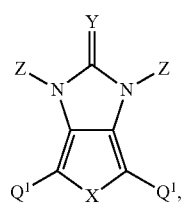

(4)

wherein each Q$^1$ is independently a halogen atom; subsequently,
(B) lithiating the compound of formula (4), to which an acid is added to obtain a compound of formula (5):

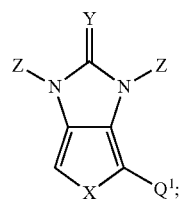

(5)

and then
(C) cross-coupling the compound of formula (5) with a compound of formula (6):

Q$^2$-W-Q$^2$ (6), wherein W is defined in claim 1, and Q$^2$ is —MgCl, —MgBr, —MgI, —ZnCl, —ZnBr, —ZnI, —Sn(R$^2$)$_3$ (wherein each R$^2$ is independently an optionally substituted alkyl group comprising 1 to 20 carbon atoms or an optionally substituted alkoxy group comprising 1 to 20 carbon atoms), a boronic acid group, or a boronic acid ester group.

5. A method for producing a π-electron conjugated compound of claim 1, the method comprising:
(A) reacting a compound of formula (3):

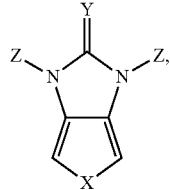

(3)

wherein X and Y are defined in claim 1, and each Z is independently an optionally substituted organic group comprising 1 to 20 carbon atoms
with $MgCl_2$, $MgBr_2$, $MgI_2$, $ZnCl_2$, $ZnBr_2$, $ZnI_2$, $Sn(R^2)_3Cl$ (wherein each $R^2$ is independently an optionally substituted alkyl group comprising 1 to 20 carbon atoms or an optionally substituted alkoxy group having 1 to 20 carbon atoms), $Sn(R^2)_3Br$, $Sn(R^2)_3I$, boronic acid, or a boronic acid ester in the presence of a base, to obtain a compound of formula (7):

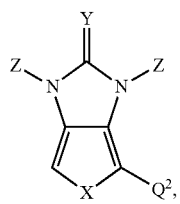

(7)

wherein $Q^2$ is —MgCl, —MgBr, —MgI, —ZnCl, —ZnBr, —ZnI, —$Sn(R^2)_3$ (wherein each $R^2$ is independently an optionally substituted alkyl group comprising 1 to 20 carbon atoms or an optionally substituted alkoxy group comprising 1 to 20 carbon atoms), a boronic acid group, or a boronic acid ester group; and then,
(B) cross-coupling the compound of formula (7) with a compound of formula (8):

$$Q^1\text{-}W\text{-}Q^1 \quad (8),$$

wherein W is defined in claim 1, and each $Q^1$ is independently a halogen atom.

6. A method for producing a π-electron conjugated compound of claim 1, the method comprising:
(A) reacting a compound of formula (9):

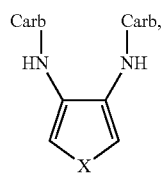

(9)

wherein X is defined in claim 1, and each Carb is independently an organic oxycarbonyl group or an organic oxythiocarbonyl group,
with a basic substance, to obtain a reaction product;
(B) reacting the reaction product with at least one compound selected from the group consisting of a magnesium compound, a zinc compound, a tin compound, a boron compound, and a halogen, to obtain a compound of formula (10):

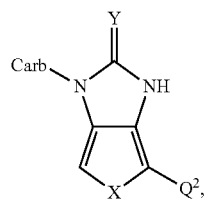

(10)

wherein Y is defined in claim 1, and $Q^2$ is —MgCl, —MgBr, —MgI, —ZnCl, —ZnBr, —ZnI, —$Sn(R^2)_3$ (wherein each $R^2$ is independently an optionally substituted alkyl group comprising 1 to 20 carbon atoms or an optionally substituted alkoxy group comprising 1 to 20 carbon atoms), a boronic acid group, and a boronic acid ester group, or an anionic compound having a structure resulting from the removal of an active proton from the compound of formula (10); and then,
(C) reacting the compound of formula (10) or the anionic compound having the structure resulting from the removal of an active proton from the compound of formula (10) with a compound of formula (8):

$$Q^1\text{-}W\text{-}Q^1 \quad (8),$$

wherein W is defined in claim 1, and each $Q^1$ is independently a halogen atom, to obtain a compound of formula (11):

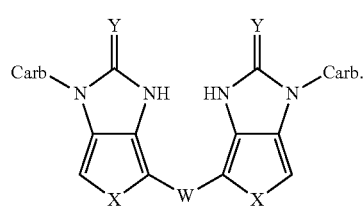

(11)

7. The method of claim 6, further comprising:
eliminating at least one Carb in the compound of formula (11).

8. The method of claim 6, further comprising:
eliminating the Carbs in the compound of formula (11), to obtain a compound of formula (12):

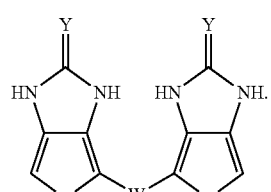

(12)

9. A method for producing a π-electron conjugated compound of claim 1, the method comprising:

(A) reacting a compound of formula (9):

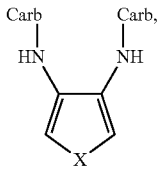

(9)

wherein X is defined in claim 1, and each Carb is independently an organic oxycarbonyl group or an organic oxythiocarbonyl group, with a basic compound, to obtain a reaction product;

(B) reacting the reaction product with at least one compound selected from the group consisting of a magnesium compound, a zinc compound, a tin compound, a boron compound, and a halogen, to obtain a compound of formula (13):

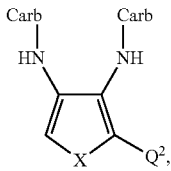

(13)

wherein $Q^2$ is —MgCl, —MgBr, —MgI, —ZnCl, —ZnBr, —ZnI, —Sn($R^2$)$_3$ (wherein each $R^2$ is independently an optionally substituted alkyl group comprising 1 to 20 carbon atoms or an optionally substituted alkoxy group comprising 1 to 20 carbon atoms), a boronic acid group, and a boronic acid ester group, or an anionic compound having a structure resulting from the removal of an active proton from the compound of formula (13);

(C) reacting the compound of formula (13) or the anionic compound having the structure resulting from the removal of an active proton from the compound of formula (13) with a compound of formula (8):

$Q^1$-W-$Q^1$ (8), wherein W is defined in claim 1, and each $Q^1$ is independently a halogen atom, to obtain a compound of formula (14):

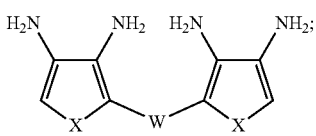

(14)

and then, (D) reacting the compound of formula (14) with a urea bond- or thiourea bond-forming compound, to obtain a compound of formula (12):

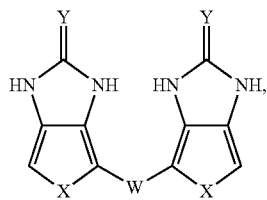

(12)

wherein Y is defined in claim 1.

10. A compound of formula (10):

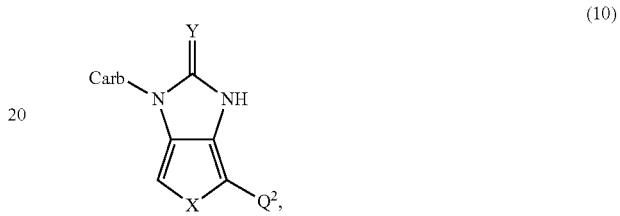

(10)

wherein:

X is an oxygen atom;

Y is an oxygen atom or a sulfur atom;

Carb is an organic oxycarbonyl group or an organic oxythiocarbonyl group; and $Q^2$ is —MgCl, —MgBr, —MgI, —ZnCl, —ZnBr, —ZnI, —Sn($R^2$)$_3$ (wherein each $R^2$ is independently an optionally substituted alkyl group comprising 1 to 20 carbon atoms or an optionally substituted alkoxy group comprising 1 to 20 carbon atoms), a boronic acid group, or a boronic acid ester group, or an anionic compound having a structure resulting from the removal of an active proton from the compound of formula (10).

11. A compound of formula (10):

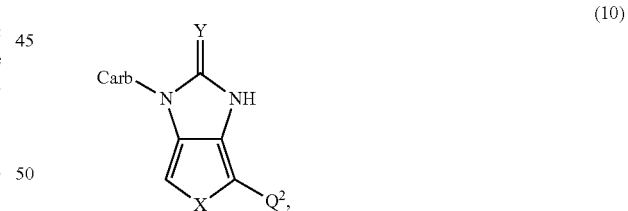

(10)

wherein:

X is —NH—;

Y is an oxygen atom or a sulfur atom;

Carb is an organic oxycarbonyl group or an organic oxythiocarbonyl group; and $Q^2$ is —MgCl, —MgBr, —MgI, —ZnCl, —ZnBr, —ZnI, —Sn($R^2$)$_3$ (wherein each $R^2$ is independently an optionally substituted alkyl group comprising 1 to 20 carbon atoms or an optionally substituted alkoxy group comprising 1 to 20 carbon atoms), a boronic acid group, or a boronic acid ester group, or an anionic compound having a structure resulting from the removal of an active proton from the compound of formula (10).

12. A compound of formula (10):

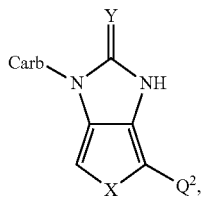
(10)

wherein:
X is —NR$^1$—, wherein R$^1$ is an optionally substituted alkyl group comprising 1 to 20 carbon atoms or an optionally substituted aryl group comprising 6 to 20 carbon atoms;
Y is an oxygen atom or a sulfur atom;
Carb is an organic oxycarbonyl group or an organic oxythiocarbonyl group; and
Q$^2$ is —MgCl, —MgBr, —MgI, —ZnCl, —ZnBr, —ZnI, —Sn(R$^2$)$_3$ (wherein each R$^2$ is independently an optionally substituted alkyl group comprising 1 to 20 carbon atoms or an optionally substituted alkoxy group comprising 1 to 20 carbon atoms), a boronic acid group, or a boronic acid ester group, or an anionic compound having a structure resulting from the removal of an active proton from the compound of formula (10).

13. A compound of formula (10):

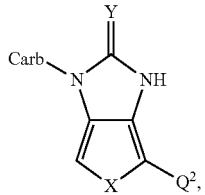
(10)

wherein:
X is an oxygen atom, a sulfur atom, —NH—, or —NR$^1$—, wherein R$^1$ is an optionally substituted alkyl group comprising 1 to 20 carbon atoms or an optionally substituted aryl group comprising 6 to 20 carbon atoms;
Y is an oxygen atom or a sulfur atom;
Carb is an organic oxycarbonyl group or an organic oxythiocarbonyl group; and
Q$^2$ is —MgCl, —MgBr, or —MgI.

14. A compound of formula (10):

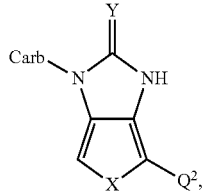
(10)

wherein:
X is an oxygen atom, a sulfur atom, —NH—, or —NR$^1$—, wherein R$^1$ is an optionally substituted alkyl group comprising 1 to 20 carbon atoms or an optionally substituted aryl group comprising 6 to 20 carbon atoms;
Y is an oxygen atom or a sulfur atom;
Carb is an organic oxycarbonyl group or an organic oxythiocarbonyl group; and
Q$^2$ is —ZnCl, —ZnBr, or —ZnI.

15. A compound of formula (10):

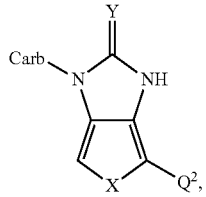
(10)

wherein:
X is an oxygen atom, a sulfur atom, —NH—, or —NR$^1$—, wherein R$^1$ is an optionally substituted alkyl group comprising 1 to 20 carbon atoms or an optionally substituted aryl group comprising 6 to 20 carbon atoms;
Y is an oxygen atom or a sulfur atom;
Carb is an organic oxycarbonyl group or an organic oxythiocarbonyl group; and
Q$^2$ is a boronic acid group or a boronic acid ester group.

* * * * *